United States Patent
Jinushi et al.

(10) Patent No.: US 9,072,230 B2
(45) Date of Patent: Jul. 7, 2015

(54) METHOD FOR PRODUCING RICE F1 SEED, RICE F1 SEED, AND RICE MALE STERILE LINE

(75) Inventors: Kenji Jinushi, Nagoya (JP); Yoichi Morinaka, Nagoya (JP); Tomonori Takashi, Kisarazu (JP); Hidemi Kitano, Nagoya (JP); Toshiro Komura, Okazaki (JP)

(73) Assignee: Honda Motor Co., Ltd., Tokyo (JP)

( * ) Notice: Subject to any disclaimer, the term of this patent is extended or adjusted under 35 U.S.C. 154(b) by 428 days.

(21) Appl. No.: 13/422,610

(22) Filed: Mar. 16, 2012

(65) Prior Publication Data

US 2012/0240285 A1 Sep. 20, 2012

(30) Foreign Application Priority Data

Mar. 18, 2011 (JP) ................................ P2011-061395

(51) Int. Cl.
*A01H 5/10* (2006.01)
*C12N 5/04* (2006.01)
*A01H 1/04* (2006.01)

(52) U.S. Cl.
CPC ... *A01H 5/10* (2013.01); *A01H 1/04* (2013.01)

(58) Field of Classification Search
USPC .................................. 800/267, 320.2, 320.1
See application file for complete search history.

(56) References Cited

U.S. PATENT DOCUMENTS

| | | | | |
|---|---|---|---|---|
| 6,512,167 | B1 * | 1/2003 | Carolo ........................ | 800/320.1 |
| 7,417,180 | B2 * | 8/2008 | Ashikari et al. .............. | 800/295 |
| 8,030,561 | B2 * | 10/2011 | Takashi et al. ............. | 800/320.2 |

FOREIGN PATENT DOCUMENTS

| | | |
|---|---|---|
| CN | 1489895 A | 4/2004 |
| CN | 1951172 A | 4/2007 |
| JP | 2005-110623 A | 4/2005 |
| JP | 2007-054020 A | 3/2007 |
| JP | 3949637 B2 | 7/2007 |
| JP | 2008-283902 A | 11/2008 |
| JP | 4248881 B2 | 1/2009 |
| JP | 4352102 B1 | 10/2009 |
| JP | 4368391 B2 | 11/2009 |
| JP | 2010-011826 A | 1/2010 |
| JP | 2010-011826 A | 1/2010 |
| JP | 2010-011842 A | 1/2010 |
| JP | 4409610 B2 | 2/2010 |
| WO | WO 02/085105 A2 | 10/2002 |
| WO | WO 03/070934 A1 | 8/2003 |
| WO | WO 2010/067801 A1 | 6/2010 |

OTHER PUBLICATIONS

Office Action issed in Chinese Application No. 201210073413.3, dated Aug. 15, 2013, 17 pages.

R⊖B (http://rgp.dna.affrc.go.jp/E/Publicdata.html) ROB.
Sugiura, et al., "Molecular Marker-assisted Selection in a Recurrent Backcross Breeding for the Incorporation of Resistance to Rice Stripe Virus and Panicle Blast in Rice (*Oryza sativa* L.," 6 pages.
Asano et al., "Genetic and Molecular Analysis of Utility of sd1 Alleles in Rice Breeding," Breeding Science 57, 2007, pp. 53-58.
Ashikari et al., "Cytokinin Oxidase Regulates Rice Grain Production," Science, vol. 309, Jul. 29, 2005, pp. 741-745.
Gu et al., "Grain quality of hybrid rice: genetic variation and molecular improvement," Accelerating Hybrid rice development, edited by Xie and Hardy, 2010, pp. 345-356.
Hayashi et al., "Durable panicle blast-resistance gene Pb1 encodes an atypical CC-NBS-LRR protein and was generated by acquiring a promoter through local genome duplication," The Plant Journal, 2010, pp. 498-510.
Kato et al., "Hybrid rice research in Japan," new development and future prospects, edited by Virmani, pp. 149-156.
Kumar et al., "Genetic analysis of waxy locus in rice (*Oryza sativa* L.)," Theor. Appl. Genet., 1987, pp. 481-488.
Kumar et al., "Inheritance of amylose content in rice (*Oryza sativa* L.)," Euphytica 38, 1998, pp. 261-269.
Liu et al., "Improvement of Resistance to Rice Blast in Zhenshan 97 by Molecular Marker-aided Selection," Acta Botanica Sinica, 2003, pp. 1346-1350.
Luo et al., "Analysis of photoperiod-sensitivity genes in Minghui 63, an restorer line of indica rice (*Oryza sativa* L.)," Sep. 2003, 1 page.
Maruyama, "Thremmatological Studies on First Filial Generation Rice Cultivar," Doctoral Dissertation of University of Tokyo, Feb. 14, 1993, 18 pages.
Miyata, et al., "Marker-assisted selection and evaluation of the QTL for stigma exsertion under japonica rice genetic background," Theor. Appl. Genet., 2006, 10 pages.
Monna et al., "Positional Cloning of Rice Semidwarfing Gene, sd-1: Rice "Green Revolution Gene" Encodes a Mutant Enzyme Involved in Gibberellin Synthesis," DNA Research 9, 2002, pp. 11-17.
Niroula et al., "Ploidy Level and Phenotypic Dissection of Nepalese Wild Species of Rice," Scientific World, vol. 3, No. 3, Jul. 2005, pp. 78-84.
Notification (Information Statement) issued in Japanese Application No. 2012-59239, mailed Nov. 26, 2013, 23 pages.
Sugiura, et al., "Molecular Marker-assisted Selection in a Recurrent Backcross Breeding for the Incorporation of Resistance to Rice Stripe Virus and Panicle Blast in Rice (*Oryza sativa* L.)," Breeding Research 6: 143-148, 2004, 6 pages.

(Continued)

*Primary Examiner* — Medina A Ibrahim
(74) *Attorney, Agent, or Firm* — Carrier Blackman & Associates, P.C.; Joseph P. Carrier; Fulchand P. Shende

(57) ABSTRACT

Provided is a method for producing a rice F1 seed including crossing a rice male sterile line of Koshihikari containing one or more genes selected from the group consisting of the Pb1 gene derived from a rice (*Oryza sativa* L) cultivar Modan and the Cr1 gene derived from *Oryza nivara*, as a seed parent, with a rice fertility restorer line as a pollen parent, and collecting the first filial generation seed (F1 seed) from the post-crossing seed parent; a rice F1 seed which is obtained by the above-described method for producing a rice F1 seed; and a rice cytoplasmic male sterile line including one or more genes selected from the group consisting of the Pb1 gene derived from rice (*Oryza sativa* L) cuitibar Modan, and the Cr1 gene derived from *Oryza nivara*.

13 Claims, 8 Drawing Sheets

(56) References Cited

OTHER PUBLICATIONS

Suzuki, "Fluctuation of Amylose Content in Rice Seeds—Mechanism and Regulation—," Agriculture and Horticulture, vol. 81, 2006, pp. 183-190.

Xu et al., "Analysis of heading time genotype for a rice photoperiod and thermo-sensitive male sterile line PeiAi64S1," Yi Chaun Xue Bao, Jan. 2005, 1 page.

Yamane et al., "Comparitive study on the genomic sequences of grain productivity related gene Gn1a regions among the gunus *Oryza*," Thremmatology study (Additional vol. 2), 2007, p. 307.

Yano et al., "Hd1, a Major Photoperiod Sensitivity Quantitative Trait Locus in Rice, Is Closely Related to the *Arabidopsis* Flowering Time Gene CONSTANS," The Plant Cell, vol. 12, Dec. 2000, pp. 2473-2483.

Yuan, "Hybrid rice breeding in China," Advancing Hybrid Rice Technology, edited by Virmani, Siddiq, Muralidharan, chapter 3, pp. 27-33.

ROB (http://rgp.dna.affrc.go.jp/E/Publicdata.html).

KOME (http://cdna01.dna.affrc.go.jp/cDNA/).

TIGR (fip://ftp.plantbiology.msu.edu/pub/data/Eukaryotic_Projects/o_sativa/annotation_dbs/pseudomolecules/).

Office Action with a mailing date of Feb. 25, 2015, issued in the corresponding CN Patent Application 201210068896.8 and the English translation thereof.

Li Ping et al., "Psysiological Bases of High Yielding Heterosis in Indica-type F1 Hybrid Rice", Scientia Agricultura Sinica, vol. 23 (5), pp. 39-44. 1990.

* cited by examiner

■ O. NIVARA-DERIVED CHROMOSOME FRAGMENT
▭ KOSHIHIKARI CHROMOSOME

■ O. NIVARA-DERIVED CHROMOSOME FRAGMENT
▭ KOSHIHIKARI CHROMOSOME

METHOD FOR PRODUCING RICE F1 SEED, RICE F1 SEED, AND RICE MALE STERILE LINE

CROSS-REFERENCE TO RELATED APPLICATION

This Application claims priority to Japanese Application No. 2011-061395, filed Mar. 18, 2011; the disclosure of which is hereby incorporated in its entirety by reference.

SEQUENCE LISTING

The instant application contains a Sequence Listing which has been submitted in ASC format via EFS-VVeb and is hereby incorporated by reference in its entirety. Said ASCII copy, created on Apr. 19, 2012, is named 17439284.txt and is 21,055 bytes in size.

BACKGROUND OF THE INVENTION

1. Field of the Invention

The present invention relates to a rice male sterile line having a favorable characteristic, a method for producing a rice F1 seed using the same rice male sterile line, and a rice F1 seed which is obtained by the same method.

2. Description of Related Art

In recent years, remarkable advancements in genome analysis techniques have enabled great improvements to be made to crop production. In particular, a DNA marker technique has showed marked progress and the construction of a new cultivar having a beneficial characteristic has become possible through such a technique. For example, up to now, tomatoes having a resistance to *Botrytis cinerea* (for example, see Patent Document 1) or rice plants (*Oryza sativa*) having improvements in lodging resistance and brown rice kernel size (for example, see Patent Document 2) have been created using DNA markers.

Further, through the use of DNA markers and the substitution of chromosome regions including valuable alleles of important genes identified hitherto, specific improvement of a desired characteristic has become possible without significant effect on a large number of other characteristics (for example, see Patent Document 3). For example, as for a rice plant, a rice plant having improvements in culm length (chromosome region in the proximity of sd1 gene), days to heading (chromosome region in the proximity of hd1 gene), number of grains per spike (chromosome region in the proximity of Gn1 gene) or the like has been created (for example, see Patent Document 4). When the sd1 gene in a chromosome of *Oryza sativa* L. cultivar Koshihikari is substituted with the sd1 gene derived from Habataki, a culm length becomes significantly shorter than *Oryza sativa* L. cultivar Koshihikari and a lodging resistance is improved. Further, when the Gn1 gene in a chromosome of *Oryza sativa* L. cultivar Koshihikari is substituted with the Gn1 gene derived from Habataki, a grain density becomes higher than *Oryza sativa* L. cultivar Koshihikari. When the hd1 gene in a chromosome of *Oryza saliva* L. cultivar Koshihikari is substituted with the hd1 gene derived from Habataki, this results in conversion to earlier growth than in *Oryza sativa* L. cultivar Koshihikari.

As for a method of creating a crop having a superior characteristic, there is an F1 hybrid breeding method in which a seed parent is deprived of an ability to synthesize pollen by using a male sterile cytoplasm or the like, whereby crossing between distantly-related lines is realized and the resulting hybrid seed is used as a cultivar. For example, with regard to *Lactuca sativa*, a *Lactuca saliva* male sterile line that can be used as a seed parent in an F1 hybrid breeding method has been created (for example, see Patent Document 5).

The F1 hybrid breeding method is used as a technique which is capable of improving yield performance to a very high level with ease by taking advantage of heterosis. Also in breeding of rice plants in Japan, application of the F1 hybrid breeding method has been attempted since the discovery of practical cytoplasmic male-sterility in 1970. In this connection, there is a history that the F1 hybrid breeding method has gradually lost its application due to the fact that taste quality of the line of rice plants reared at that time was not sufficiently high, and a need regarding the high-yielding ability of a rice plant during the rice oversupply period since then is lower.

However, increasing a yield potential of crops has recently become important again in terms of increasing production of food, cultivation costs, and efficient utilization of input energy during cultivation, and will become a more important breeding goal from now on. Further, enlarging a plant itself through the enhancement of productive capacity leads to an increase in productivity of crop residues attracting attention as a raw material of bioethanol of the second generation, and through relative reduction of an amount of GHG discharged in the course of growing processes of crops, may also contribute to a solution to energy problems and environmental problems.

Under the present circumstances in which an improvement of a yield potential has become considered important, an F1 hybrid breeding technique has increasingly gained interest. With regard to an F1 hybrid breeding method, there is a need to create F1 hybrids between large numbers of lines for a candidate line to be selected in a combinatorial test, and therefore the selection of a male sterile line serving as a seed parent has become highly important so as to maintain high efficiency of selection.

*Oryza saliva* L. cultivar Koshihikari, which is the leading variety in Japan, is evaluated highly regarding taste quality, and the line obtained using Koshihikari as a rearing seed parent has a large number of lines with good taste quality. In addition to taste quality, as shown by the fact that it is most widely cultivated in Japan, Koshihikari has adaptability of cultivation over a wide area and exhibits a great number of excellent characteristics such as germination of strong shoots. Further, since Koshihikari has been used as a study subject in a variety of experiments, Koshihikari has an accumulation of scientific knowledge and has an advantage from the viewpoint that it is easy to find leads for improvement. Taken together, it can be said that Koshihikari is one of the most promising lines in rearing of a seed parent of an F1 hybrid.

PRIOR ART DOCUMENTS

Patent Documents

Patent Document 1: Japanese Patent No. 4248881
Patent Document 2: Japanese Patent No. 4368391
Patent Document 3: Japanese Patent No. 4409610
Patent Document 4: Japanese Patent No. 4352102
Patent Document 5: Japanese Patent No. 3949637

SUMMARY OF THE INVENTION

However, where an F1 hybrid is reared using Koshihikari as one parent, problems frequently occur. For example, since Koshihikari exhibits susceptibility to rice blast, an F1 line obtained from a male sterile line of Koshihikari also exhibits frequent appearance of a line susceptible to rice blast, which consequently leads to significant deterioration in efficiency of selection.

Further, an F1 hybrid using a male sterile line of Koshihikari has a problem of low seed production efficiency.

An object of the present invention is to provide a male sterile line of Koshihikari which is highly suitable in an F1 hybrid breeding method, and a method for producing a rice F1 seed using the same rice male sterile line.

As a result of extensive and intensive studies to solve the above-mentioned problems, the present inventors have found that a superior F1 hybrid can be more efficiently created by using a male sterile line having rice blast resistance or a male sterile line having a high stigma exsertion rate as a seed parent. The present invention has been completed based on this finding.

Specifically, the present invention provides:

(1) A method for producing a rice F1 seed, including crossing a rice male sterile line containing one or more genes selected from the group consisting of the Pb1 gene derived from a rice (*Oryza sativa* L) cultivar Modan and the Cr1 gene derived from *Oryza nivara*, as a seed parent, with a rice fertility restorer line as a pollen parent, and collecting a first filial generation seed (F1 seed) from the post-crossing seed parent, (2) The method for producing a rice F1 seed according to (1), wherein the rice male sterile line further contains one or more genes selected from the group consisting of the sd1 gene derived from *Oryza sativa* L. cultivar Habataki, the Gn1 gene derived from *Oryza sativa* L. cultivar Habataki, and the hd1 gene derived from *Oryza sativa* L. cultivar Habataki, (3) The method for producing a rice F1 seed according to (1) or (2), wherein the rice male sterile line further exhibits semi-waxiness, (4) The method for producing a rice F1 seed according to (1), wherein the rice male sterile line is a cytoplasmic male sterile line selected from the group consisting of a rice cytoplasmic male sterile line JMS-019 (*Oryza sativa* L. cultivar JMS-019), a rice cytoplasmic male sterile line JMS-020, a rice cytoplasmic male sterile line JMS-021, a rice cytoplasmic male sterile line JMS-022, a rice cytoplasmic male sterile line JMS-023, and a rice cytoplasmic male sterile line JMS-024, (5) A rice F1 seed which is obtained by the method for producing a rice F1 seed of any one of (1) to (4), (6) A rice F1 hybrid line Hybrid Togo 1go,
(7) A rice F1 hybrid line Hybrid Togo 2go,
(8) A rice F1 hybrid line Hybrid Togo 3go,
(9) A rice F1 hybrid line Hybrid Togo 4go,

(10) A rice male sterile line containing one or more genes selected from the group consisting of the Pb1 gene derived from rice (*Oryza sativa* L) cultivar Modan, and the Cr1 gene derived from *Oryza nivara*,

(11) The rice male sterile line according to (10), further containing one or more genes selected from the group consisting of the sd1 gene derived from *Oryza saliva* L. cultivar Habataki, the Gn1 gene derived from *Oryza sativa* L. cultivar Habataki, and the hd1 gene derived from *Oryza sativa* L. cultivar Habataki,

(12) The rice male sterile line according to (10) or (11), further exhibiting semi-waxiness,

(13) A rice cytoplasmic male sterile line JMS-019 (*Oryza sativa* L. cultivar JMS-019),

(14) A rice cytoplasmic male sterile line JMS-020 (*Oryza sativa* L. cultivar JMS-020),

(15) A rice cytoplasmic male sterile line JMS-021 (*Oryza sativa* L. cultivar JMS-021),

(16) A rice cytoplasmic male sterile line JMS-022 (*Oryza sativa* L. cultivar JMS-022),

(17) A rice cytoplasmic male sterile line JMS-023 (*Oryza sativa* L. cultivar JMS-023),

(18) A rice cytoplasmic male sterile line JMS-024 (*Oryza sativa* L. cultivar JMS-024),

(19) A rice near-isogenic line containing the Cr1 gene derived from *Oryza nivara* as a foreign gene.

The method for producing a rice F1 seed in accordance with the present invention employs a rice male sterile line with improvement of a specific characteristic as a seed parent and is therefore capable of producing an F1 hybrid seeds having such a characteristic. In particular, the rice male sterile line used in the present invention is improved in at least one of rice blast resistance and seed production efficiency and is therefore capable of producing a seed of a rice F1 hybrid with higher efficiency of selection than the case of where a male sterile line of *Oryza sativa* L. cultivar Koshihikari is used as a seed parent.

DETAILED DESCRIPTION OF THE INVENTION

Figure 1:
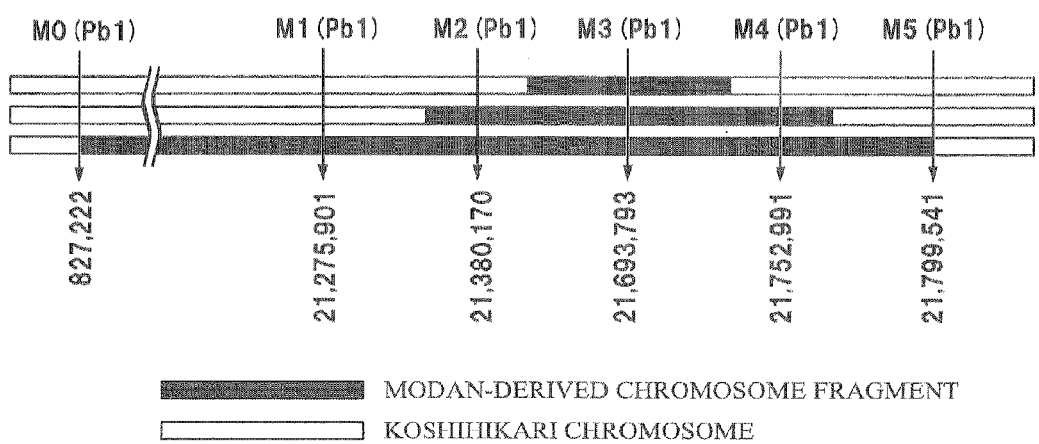
FIG. 1 is a view showing a DNA marker (SNP) of approximately 21.38 Mbp in which the Pb1 gene in the chromosome 11 of rice is encoded.

In the present invention, the term "near-isogenic line" means a line in which only a part of a chromosome of an original cultivar is substituted with a chromosome fragment derived from a foreign cultivar. The foreign cultivar is not particularly limited as long as it is a cultivar other than an original cultivar, and may be a cultivar of a plant which is the same species as that of an original cultivar, may be a cultivar of a plant which is a different species from that of an original cultivar, and may be a cultivar other than a plant such as an animal. In the present invention, the term "cultivar" means a population which is the same species of a plant, but can be clearly discriminated from other species in the same species in a certain characteristic, due to different genetic constitution.

The DNA markers in the present invention are not particularly limited as long as they can discriminate between a chromosome derived from an original cultivar and a chromosome derived from a foreign cultivar, that is, they can detect a difference in a DNA sequence on a chromosome between the original cultivar and the foreign cultivar, and a DNA marker which is conventionally used in the gene analysis field may be used. These DNA markers may be, for example, a marker which can detect gene polymorphism such as SNP (Single Nucleotide Polymorphism) or a difference in the repetition number of SSR (Simple Sequence Repeats), or may be a RFLP (Restriction Fragment Length Polymorphism) marker. Discrimination between an allele derived from the original cultivar and an allele derived from the foreign cultivar using these DNA markers may be carried out by a conventional method. For example, PCR is carried out as follows: employing DNA extracted from each individual as a template; and using primers which are capable of specifically hybridizing with particular SNP and SSR. Then, by detecting the presence or the absence of the PCR product using an electrophoresis method or the like, each polymorphism may be discriminated. Alternatively, by detecting a pattern of a DNA fragment using an electrophoresis method or the like after DNA extracted from each individual is treated with a restriction enzyme, each polymorphism may be discriminated. Primers which are capable of specifically hybridizing with particular SNP or SSR may be designed by a conventional method using a primer design tool which is generally used, depending on a nucleotide sequence of SNP and SSR. In addition, designed primers may be synthesized using any method well-known in the art.

A known DNA marker may be optionally used as the DNA marker. Alternatively, the DNA marker may be a newly prepared DNA marker. For example, when a known DNA marker regarding rice is used, SNP markers disclosed in the pamphlet of International Publication No. WO 2003/070934, and DNA markers published in Rice Genome Research Program may be used.

Genetic information of each cultivar is available, for example, from the National Center for Biotechnology Information (NCBI) or the DNA Data Bank of Japan (DDBJ), which are international nucleotide sequence databases. Particularly, genetic information of each cultivar of rice is available in Knowledge-based Oryza Molecular Biological Encyclopedia.

In the present invention and the present specification, "the $X^{th}$ base of a chromosome of *Oryza sativa* L. cultivar Nipponbare" is a region which is determined based on the base sequence of genomic DNA of *Oryza sativa* L. cultivar Nipponbare (version 2) published in The Institute for Genomic Research.

In the present invention and the present specification, the term "region corresponding to a region from the $X^{th}$ base to the $Y^{th}$ base of a chromosome of *Oryza sativa* L. cultivar Nipponbare" refers to a region in a chromosome of a rice individual, which exhibits a high homology with the region from the $X^{th}$ base to the $Y^{th}$ base of a chromosome of *Oryza sativa* L. cultivar Nipponbare, and may be determined in such a manner that the base sequence of a known genomic DNA of *Oryza sativa* L. cultivar Nipponbare and the base sequence of a genomic DNA of the rice individual are aligned to make the highest homology therebetween. The term "SNP corresponding to SNP of *Oryza sativa* L. cultivar Nipponbare" in a rice individual other than *Oryza sativa* L. cultivar Nipponbare refers to, in a region containing the SNP, a base at the position corresponding to the SNP when the base sequence of a known genomic DNA of *Oryza sativa* L. cultivar Nipponbare and the base sequence of a genomic DNA of the rice individual are aligned to make the highest homology therebetween.

The method for producing a rice F1 seed in accordance with the present invention includes crossing a male sterile line of *Oryza sativa* L. cultivar Koshihikari having an improved specific characteristic as a seed parent with a rice fertility restorer line as a pollen parent, and collecting the first filial generation seed (F1 seed) from the post-crossing seed parent.

First, a rice male sterile line used in the present invention will be described. The rice male sterile line used in the present invention is a male sterile line of a near-isogenic line in which a specific characteristic is improved through the substitution of a part of a chromosome of *Oryza sativa* L. cultivar Koshihikari with a chromosome fragment derived from a foreign cultivar.

The male sterile line of a near-isogenic line may be created by a conventional method. For example, a Koshihikari cytoplasmic male sterile line having the same characteristic as *Oryza sativa* L. cultivar Koshihikari except that it is of cytoplasmic male sterility is crossed with a near-isogenic line of *Oryza sativa* L. cultivar Koshihikari in which a desired region is substituted with a chromosome fragment derived from foreign cultivar, and the resulting F1 hybrid is subjected to continuous backcrossing using a near-isogenic line of the *Oryza sativa* L. cultivar Koshihikari as a pollen parent, whereby a rice cytoplasmic male sterile line having the same characteristic as a near-isogenic line of the *Oryza sativa* L. cultivar Koshihikari except that it is of cytoplasmic male sterility may be obtained. In addition, a Koshihikari cytoplasmic male sterile line may be created, for example, by crossing an *Oryza sativa* L. cultivar Koshihikari and a rice cytoplasmic male sterile line, and repeatedly backcrossing the resulting F1 hybrid, using an *Oryza sativa* L. cultivar Koshihikari as a pollen parent. The rice cytoplasmic male sterile line is not particularly limited as long as it is a gramineous cultivar exhibiting cytoplasmic male sterility. Examples of the rice cytoplasmic male sterile line include *Oryza sativa* L. cultivar CHINSURAH BORO 2 which is of BT-type cytoplasmic male sterility, *Oryza sativa* L. cultivar Male sterile wild rice which is of WA-type cytoplasmic male sterility, *Oryza sativa*

L. cultivar Gambiaca which is of GA-type cytoplasmic male sterility, and *Oryza sativa* L. cultivar Dissi which is of Di-type cytoplasmic male sterility.

Further, the male sterile line of a near-isogenic line may be an environmental condition-dependent male sterile line due to a mutant gene leading to sterility under specific environmental conditions. Examples of the environmental condition-dependent male sterile line include a photoperiod-sensitive genic male sterile (PGMS) line using a PMS1 gene or PMS2 gene leading to male sterility under long-day conditions, and a thermo-sensitive genic male sterile (TGMS) line using a TMS1 gene or TMS2 gene leading to male sterility under high temperature conditions. A rice male sterile line having the same characteristic as a near-isogenic line of the *Oryza sativa* L. cultivar Koshihikari except that it exhibits environmental condition-dependent male sterility due to the mutant gene may be obtained by crossing a near-isogenic line of *Oryza sativa* L. cultivar Koshihikari with an environmental condition-dependent male sterile line having such a mutant gene, and subjecting the resulting F1 hybrid to continuous backcrossing using the near-isogenic line of *Oryza sativa* L. cultivar Koshihikari as a pollen parent.

The foreign cultivar-derived chromosome fragment being inserted in a near-isogenic line of *Oryza sativa* L. cultivar Koshihikari is not particularly limited as long as insertion of the chromosome fragment results in more improvement of a specific characteristic than *Oryza sativa* L. cultivar Koshihikari. For example, it is sufficient that the foreign cultivar-derived chromosome fragment to be inserted contains a region encoding a gene directly contributing to desired characteristic improvement (causative gene). The foreign cultivar-derived chromosome fragment may be a region containing only a causative gene, or a region containing the causative gene and other genes (for example, a region consisting of 14.6 Mbp to 29.2 Mbp in length).

In the present invention and the present specification, the term ""Y" gene derived from *Oryza sativa* L. cultivar "X"" is intended to encompass a "Y" gene derived from *Oryza saliva* L. cultivar "X" itself (that is, a "Y" gene present in a chromosome of *Oryza saliva* L. cultivar "X"), as well as a "Y" gene derived from *Oryza saliva* L. cultivar having a "Y" gene substantially identical to that of *Oryza saliva* L. cultivar "X". This is because the same effect as in the present invention is exhibited even when, in place of a "Y" gene derived from *Oryza sativa* L. cultivar "X", a "Y" gene derived from *Oryza sativa* L. cultivar other than *Oryza sativa* L. cultivar "X", which is substantially identical to a "Y" gene derived from *Oryza saliva* L. cultivar "X", is incorporated into a chromosome. Here, the "Y" gene substantially identical to a "Y" gene derived from *Oryza sativa* L. cultivar "X" refers to a "Y" gene which is derived from *Oryza sativa* L. cultivar other than *Oryza sativa* L. cultivar "X" and has a function virtually equivalent to that of a "Y" gene derived from *Oryza sativa* L. cultivar "X". Specific examples thereof include an *Oryza sativa* L. cultivar, which is a posterity cultivar of *Oryza saliva* L. cultivar "X" and has inherited alleles of a "Y" gene-containing region from *Oryza saliva* L. cultivar "X", an *Oryza sativa* L. cultivar, which corresponds to an ancestor of *Oryza sativa* L. cultivar "X" and has alleles of a "Y" gene-containing region in common in *Oryza sativa* L. cultivar "X", and an *Oryza sativa* L. cultivar into which a chromosome fragment of a "Y" gene-containing region contained in *Oryza sativa* L. cultivar having a "Y" gene substantially identical to that of these *Oryza saliva* L. cultivar "X" has been incorporated.

That is, in the present invention and the present specification, unless otherwise specifically indicated, the term "Pb1 gene derived from *Oryza saliva* L. cultivar Modan" is intended to encompass a Pb1 gene derived from *Oryza sativa* L. cultivar Madan itself as well as a Pb1 gene substantially identical to that gene, for example, a Pb1 gene derived from *Oryza sativa* L. cultivar such as *Oryza sativa* L. cultivar Koshihikari SBL, *Oryza saliva* L. cultivar Aichinokaori, *Oryza sativa* L. cultivar SBL, *Oryza sativa* L. cultivar Aoinokaze, *Oryza sativa* L. cultivar Asahinoyume, *Oryza sativa* L. cultivar Matsuribare, *Oryza sativa* L. cultivar Tsukinohikari, *Oryza sativa* L. cultivar Asanohikari, *Oryza saliva* L. cultivar Akanesora, *Oryza sativa* L. cultivar Goropikari, *Oryza saliva* L. cultivar Koigokoro, or *Oryza sativa* L. cultivar Daichinokaze.

Similarly, in the present invention and the present specification, unless otherwise specifically indicated, the term "sd1 gene derived from *Oryza sativa* L. cultivar Habataki" is intended to encompass an sd1 gene derived from *Oryza saliva* L. cultivar Habataki itself as well as an sd1 gene substantially identical to that gene, for example, an sd1 gene derived from *Oryza sativa* L. cultivar such as *Oryza sativa* L. cultivar Dee-Geo-Woo-Gen, *Oryza sativa* L. cultivar IR8, *Oryza sativa* L. cultivar Kinuhikari, *Oryza sativa* L. cultivar Yumehitachi, *Oryza sativa* L. cultivar Koshihikari eichi 4go, *Oryza sativa* L. cultivar Koshihikari kazusa 2go, *Oryza sativa* L. cultivar Koshihikari kazusa ago, or *Oryza sativa* L. cultivar Koshihikari kazusa 4go.

Similarly, in the present invention and the present specification, unless otherwise specifically indicated, the term "Gn1 gene derived from *Oryza sativa* L. cultivar Habataki" is intended to encompass a Gn1 gene derived from *Oryza sativa* L. cultivar Habataki itself as well as a Gn1 gene substantially identical to that gene, for example, a Gn1 gene derived from *Oryza sativa* L. cultivar such as *Oryza saliva* L. cultivar Koshihikari eichi 2go, *Oryza sativa* L. cultivar Koshihikari kazusa 2go, *Oryza sativa* L. cultivar Koshihikari kazusa 3go, or *Oryza sativa* L. cultivar Koshihikari kazusa 4go.

Similarly, in the present invention and the present specification, unless otherwise specifically indicated, the term "hd1 gene derived from *Oryza sativa* L. cultivar Habataki" is intended to encompass an hd1 gene derived from *Oryza sativa* L. cultivar Habataki itself as well as an hd1 gene substantially identical to that gene, for example, an hd1 gene derived from *Oryza saliva* L. cultivar such as *Oryza sativa* L. cultivar Koshihikari eichi 3go, *Oryza sativa* L. cultivar Koshihikari kazusa 1go, *Oryza sativa* L. cultivar Koshihikari kazusa 2go, or *Oryza sativa* L. cultivar Koshihikari kazusa 4go.

In the present invention, a rice male sterile line containing one or more genes selected from the group consisting of a Pb1 gene derived from *Oryza saliva* L. cultivar Modan, and a Cr1 gene derived from *Oryza nivara* is employed as a seed parent. The seed parent may be a rice male sterile line containing at least one of a Pb1 gene derived from *Oryza sativa* L. cultivar Modan, and a Cr1 gene derived from *Oryza nivara*, or may be a rice male sterile line containing both genes.

The Pb1 gene is present in the chromosome 11 of a rice plant. Rice blast resistance of *Oryza sativa* L. cultivar Koshihikari may be increased by the insertion of the Pb1 gene derived from *Oryza sativa* L. cultivar Modan into *Oryza sativa* L. cultivar Koshihikari. Meanwhile, the Cr1 gene is present in the chromosome 3 of a rice plant, and a stigma exsertion rate of *Oryza sativa* L. cultivar Koshihikari may be increased by the insertion of the Cr1 gene derived from *Oryza nivara* into *Oryza sativa* L. cultivar Koshihikari.

The rice male sterile line containing the Pb1 gene derived from *Oryza sativa* L. cultivar Modan (Modan-derived Pb1-containing rice male sterile line) may be created from a near-isogenic line of *Oryza sativa* L. cultivar Koshihikari where a region in which the Pb1 gene in a chromosome of *Oryza sativa* L. cultivar Koshihikari is encoded has been substituted with a chromosome fragment containing a region encoding the Pb1 gene derived from *Oryza sativa* L. cultivar Modan (Modan-derived Pb1-containing near-isogenic line) and a Koshihikari male sterile line, according to the above-mentioned method. The Modan-derived chromosome fragment contained in the Modan-derived Pb1-containing near-isogenic line is not particularly limited as long as it contains a region in which the Pb1 gene is encoded, and may contain only the region in which the Pb1 gene is encoded, and a gene present in the proximity of the Pb1 gene, together with the Pb1 gene, may also be inserted into *Oryza sativa* L. cultivar Koshihikari. FIG. 1 shows a DNA marker (SNP) of approximately 21.38 Mbp in which the Pb1 gene in the chromosome 11 of rice is encoded. A length of the Modan-derived chromosome fragment may be determined by using a DNA marker. For example, as shown in FIG. 1, in the Modan-derived Pb1-containing near-isogenic line, an end on an upstream side of the inserted Modan-derived chromosome fragment may be present between SNP corresponding to SNP at the position of 21,380,170 in the chromosome 11 of *Oryza sativa* L. cultivar Nipponbare (G in *Oryza sativa* L. cultivar Koshihikari, and A in *Oryza sativa* L. cultivar Modan) (hereinafter, referred to as "SP-5290") and SNP corresponding to SNP at the position of 21,693,793 in the chromosome 11 of *Oryza sativa* L. cultivar Nipponbare (A in *Oryza sativa* L. cultivar Koshihikari, and G in *Oryza saliva* L. cultivar Modan) (hereinafter, referred to as "SP-5384"), and an end on a downstream side of the Modan-derived chromosome fragment may be present between SP-5384 and SNP corresponding to SNP at the position of 21,752,991 in the chromosome 11 of *Oryza sativa* L. cultivar Nipponbare (T in *Oryza sativa* L. cultivar Koshihikari, and C in *Oryza sativa* L. cultivar Modan) (hereinafter, referred to as "SP-5569") (top in FIG. 1). Alternatively, an end on an upstream side of the Modan-derived chromosome fragment may be present between SNP corresponding to SNP at the position of 21,275,901 in the chromosome 11 of *Oryza sativa* L. cultivar Nipponbare (T in *Oryza sativa* L. cultivar Koshihikari, and C in *Oryza sativa* L.

cultivar Modan) (hereinafter, referred to as "SP-4234") and SP-5290, and an end on a downstream side of the Modan-derived chromosome fragment may be present between SP-5569 and SNP corresponding to SNP at the position of 21,799,541 in the chromosome 11 of *Oryza sativa* L. cultivar Nipponbare (C in *Oryza sativa* L. cultivar Koshihikari, and T in *Oryza sativa* L. cultivar Modan) (hereinafter, referred to as "SP-4236") (middle in FIG. 1). Further, a longer region, containing a region encoding the Pb1 gene derived from *Oryza sativa* L. cultivar Modan, may be substituted with the Modan-derived chromosome fragment. For example, the region containing a region of approximately 21.0 Mbp ranging from SNP corresponding to SNP at the position of 827,222 in the chromosome 11 of *Oryza sativa* L. cultivar Nipponbare (G in *Oryza sativa* L. cultivar Koshihikari G, and A in *Oryza sativa* L. cultivar Modan) (hereinafter, referred to as "SP-2650") to SP-4236 may be substituted with the Modan-derived chromosome fragment (bottom in FIG. 1). Base sequences of individual DNA markers and primers usable in discrimination are shown in Table 1.

TABLE 1

| Marker | | Position in the chromosome 11 | Type | Sequence | SEQ ID NO: |
|---|---|---|---|---|---|
| M0(Pb1) | SP-2650 | 827,222 | Ga | Upper Seq: GCTAATACCTTCCTATGAAAGCTC | 1 |
| | | | | Lower Seq: CGCTCTGCAAAAGGCAAG | 2 |
| | | | | SNP primer: GTGTGTAATTGGAGACAAAGCA | 3 |
| M1(Pb1) | SP-4234 | 21,275,901 | Tc | Upper Seq: AGCTATCTCCAGATCTGAGC | 4 |
| | | | | Lower Seq: CCGATACTACGATACGATCC | 5 |
| | | | | SNP primer: CTTGCTTATGACGTGGCATG | 6 |
| M2(Pb1) | SP-5290 | 21,380,170 | Ga | Upper Seq: CTAACCTTGCAAATGTTGTGCC | 7 |
| | | | | Lower Seq: CAGTAAGTTCAGTGATGTTGCC | 8 |
| | | | | SNP primer: CCTTAACCTGGGGCAGCTCAGT | 9 |
| M3(Pb1) | SP-5384 | 21,693,793 | Ag | Upper Seq: TTCGCTTTTTCCTCCAGCTC | 10 |
| | | | | Lower Seq: TAGCATGAAGAGGAGTAGGG | 11 |
| | | | | SNP primer: TACTCCTAAATCGCCACATG | 12 |
| M4(Pb1) | SP-5569 | 21,752,991 | Tc | Upper Seq: GTTGGTGCAATACATAGACC | 13 |
| | | | | Lower Seq: TACTGATCTGGCTCATGCAG | 14 |
| | | | | SNP primer: ACAATGGCCAGATTGTGTCC | 15 |
| M5(Pb1) | SP-4236 | 21,799,541 | Ct | Upper Seq: AAGCACAAGGCTTCTCGAGG | 16 |
| | | | | Lower Seq: GCAGGAATTTGATTCTCCTGGG | 17 |
| | | | | SNP primer: CTTTCTACGACTGTTGATACGGT | 18 |

Figure 2:
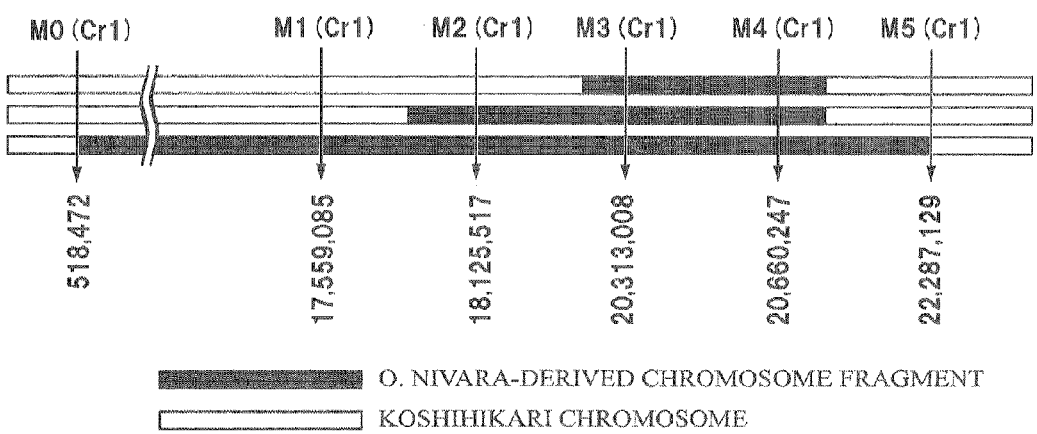
FIG. 2 is a view showing a DNA marker (SNP) of approximately 21 Mbp in which the Cr1 gene in the chromosome 3 of rice is encoded.

The rice male sterile line containing the Cr1 gene derived from *Oryza nivara* (*O. nivara*-derived Cr1-containing rice male sterile line) may be created by a near-isogenic line of *Oryza sativa* L. cultivar Koshihikari where a region in which the Cr1 gene in a chromosome of *Oryza sativa* L. cultivar Koshihikari is encoded has been substituted with a chromosome fragment containing a region encoding the Cr1 gene derived from *Oryza nivara* (*O. nivara*-derived Cr1-containing near-isogenic line) and a Koshihikari male sterile line, according to the above-mentioned method. The *O. nivara*-derived chromosome fragment contained in the *O. nivara*-derived Cr1-containing near-isogenic line is not particularly limited as long as it contains a region in which the Cr1 gene is encoded, and may contain only the region in which the Cr1 gene is encoded, and a gene present in the proximity of the Cr1 gene, together with the Cr1 gene, may also be inserted into *Oryza saliva* L. cultivar Koshihikari. FIG. 2 shows a DNA marker (SNP) of approximately 21 Mbp in which the Cr1 gene in the chromosome 3 of rice is encoded. A length of the *O. nivara*-derived chromosome fragment may be determined by using a DNA marker. For example, as shown in FIG. 2, in the *O. nivara*-derived Cr1-containing near-isogenic line, an end on an upstream side of the inserted *O. nivara*-derived chromosome fragment may be present between SNP corresponding to SNP at the position of 18,125,517 in the chromosome 3 of *Oryza sativa* L. cultivar Nipponbare (A in *Oryza sativa* L. cultivar Koshihikari, and G in rice cultivar *O. nivara*) (hereinafter, referred to as "SP-4141") and SNP corresponding to SNP at the position of 20,313,008 in the chromosome 3 of *Oryza sativa* L. cultivar Nipponbare (T in *Oryza sativa* L. cultivar Koshihikari, and C in rice cultivar *O. nivara*) (hereinafter, referred to as "SP-3823"), and an end on a downstream side of the *O. nivara*-derived chromosome fragment may be present between SNP corresponding to SNP at the position of 20,660,247 in the chromosome 3 of *Oryza sativa* L. cultivar Nipponbare (A in *Oryza sativa* L. cultivar Koshihikari, and G in rice cultivar *O. nivara*) (hereinafter, referred to as "SP-3826") and SNP corresponding to SNP at the position of 22,287,129 in the chromosome 3 of *Oryza sativa* L. cultivar Nipponbare (T in *Oryza sativa* L. cultivar Koshihikari, and G in rice cultivar *O. nivara*) (hereinafter, referred to as "SP-306") (top in FIG. 2). Alternatively, an end on an upstream side of the *O. nivara*-derived chromosome fragment may be present between SNP corresponding to SNP at the position of 17,559,085 in the chromosome 3 of Nipponbare (T in *Oryza sativa* L. cultivar Koshihikari, and G in rice cultivar *O. nivara*) (hereinafter, referred to as "SP-3819") and SP-4141, and an end on a downstream side of the *O. nivara*-derived chromosome fragment may be present between SP-3826 and SP-306 (middle in FIG. 2). Further, a longer region, containing a region encoding the Cr1 gene derived from rice cultivar *O. nivara*, may be substituted with the *O. nivara*-derived chromosome fragment. For example, the region containing a region of approximately 21.8 Mbp ranging from SNP corresponding to SNP at the position of 518, 472 in the chromosome 3 of *Oryza sativa* L. cultivar Nipponbare (A in *Oryza sativa* L. cultivar Koshihikari, and G in rice cultivar *O. nivara*) (hereinafter, referred to as "SP-2966") to SP-306 may be substituted with the *O. nivara*-derived chromosome fragment (bottom in FIG. 2). Base sequences of individual DNA markers and primers usable in discrimination are shown in Table 2.

The rice male sterile line containing both the Pb1 gene derived from *Oryza saliva* L. cultivar Modan and the Cr1 gene derived from *Oryza nivara* (Modan-derived. Pb1/*O. nivara*-derived Cr1-containing rice male sterile line) may be created from a near-isogenic line of *Oryza sativa* L. cultivar Koshihikari where a region in which the Pb1 gene in a chromosome of *Oryza sativa* L. cultivar Koshihikari is encoded has been substituted with a chromosome fragment containing a region encoding the Pb1 gene derived from *Oryza saliva* L. cultivar Modan, and a region in which the Cr1 gene in a chromosome of *Oryza sativa* L. cultivar Koshihikari is encoded has been substituted with a chromosome fragment containing a region encoding the Cr1 gene derived from *Oryza nivara* (Modan-derived Pb1/*O. nivara*-derived Cr1-containing near-isogenic line), and a Koshihikari male sterile line, according to the above-mentioned method. The Modan-derived Pb1/*O. nivara*-derived Cr1-containing near-isogenic line may be created, for example, by crossing a Modan-derived Pb1-containing near-isogenic line and an *O. nivara*-derived Cr1-containing near-isogenic line, and selecting an individual where the region in which the Pb1 gene is encoded is a region derived from *Oryza sativa* L. cultivar Modan and the region in which the Cr1 gene is encoded is a region derived from *O. nivara*, in homologous chromosomes of both parties, using a DNA marker as an indicator, from the second filial generation (F2 hybrid) obtained by self-mating the resulting F1 hybrid.

The rice fertility restorer line used as a pollen parent in the method for producing a rice F1 seed in accordance with the present invention is not particularly limited as long as it is a rice plant line which is capable of restoring fertility of a rice male sterile line used as a seed parent. Where the seed parent is of BT-type cytoplasmic male sterility, examples of the rice fertility restorer line include *Oryza saliva* L. cultivar JFR-004, *Oryza saliva* L. cultivar ST-1, *Oryza sativa* L. cultivar ST-2, *Oryza saliva* L. cultivar ST-4, *Oryza sativa* L. cultivar Takanari, *Oryza sativa* L. cultivar Guichao 2, *Oryza sativa* L. cultivar Shui-Yuan 258, and *Oryza sativa* L. cultivar Habataki. Further, whether or not a certain *Oryza sativa* L. cultivar is a rice fertility restorer line for a certain Koshihikari male sterile line may be investigated by crossing this *Oryza saliva* L. cultivar and the Koshihikari male sterile line, and examining male fertility of the resulting F1 hybrid. In the case

TABLE 2

| Marker | | Position in the chromosome 3 | Type | Sequence | SEQ ID NO: |
|---|---|---|---|---|---|
| M0(Cr1) | SP-2966 | 518,472 | Ag | Upper Seq: ACTAGAGGAGCACTGCAG | 19 |
| | | | | Lower Seq: CATGCCTGCATTCCTGCT | 20 |
| | | | | SNP primer: ACAGGCAAACGTTGCCTCG | 21 |
| M1(Cr1) | SP-3819 | 17,559,085 | Tg | Upper Seq: GGTTTGTGCTGGTCATGGC | 22 |
| | | | | Lower Seq: ACTAACCATAACGCGAGCCT | 23 |
| | | | | SNP primer: TCCCAGATCGAATCGAG | 24 |
| M2(Cr1) | SP-4141 | 18,125,517 | Ag | Upper Seq: CTAGCGTGGGCAATGACTA | 25 |
| | | | | Lower Seq: CTAAACCGAGGTGGCTAG | 26 |
| | | | | SNP primer: ATCTGGTAGCTGATCAACCC | 27 |
| M3(Cr1) | SP-3823 | 20,313,008 | Tc | Upper Seq: TGCTGCATAAGCGTACATGG | 28 |
| | | | | Lower Seq: GAACCAATGGAATGCTGGCT | 29 |
| | | | | SNP primer: GGATATGATCCATATGGTTATG | 30 |
| M4(Cr1) | SP-3826 | 20,660,247 | Ag | Upper Seq: CATCTTGCGGTTGTAGTTGG | 31 |
| | | | | Lower Seq: CAAGGAGGAAAATATGCCAGCA | 32 |
| | | | | SNP primer: ATCGAGAATATCACAATGCG | 33 |
| M5(Cr1) | SP-306 | 22,287,129 | Tg | Upper Seq: CATATTCTACAGCGTTCTCGTC | 34 |
| | | | | Lower Seq: AACACCAAGGGCGATCGAG | 35 |
| | | | | SNP primer: ATACCGAGCCCAGCAAT | 36 | where male sterility has been restored in the F1 hybrid, the *Oryza sativa* L. cultivar is found to be a rice fertility restorer line for the Koshihikari male sterile line. Further, in the case where the seed parent is of an environmental condition-dependent male sterile line, any rice line may be used as a rice fertility restorer line as long as it is a rice plant line not containing a mutant gene responsible for male sterility that the seed parent has possessed. This is because the mutant gene does not express a mutant characteristic in F1 (hetero state).

The Modan-derived Pb1-containing rice male sterile line, *O. nivara*-derived Cr1-containing rice male sterile line, Modan-derived Pb1/*O. nivara*-derived Cr1-containing rice male sterile line, rice fertility restorer line or the like used in the present invention may be a line newly created by the above-mentioned method or may be a conventional line.

F1 seeds are obtained by crossing the Modan-derived Pb1-containing rice male sterile line, *O. nivara*-derived Cr1-containing rice male sterile line or Modan-derived Pb1/*O. nivara*-derived Cr1-containing rice male sterile line as a seed parent with a rice fertility restorer line as a pollen parent. The crossing may be carried out by natural mating or artificial mating.

A rice male sterile line containing the Modan-derived Pb1 gene is excellent in terms of rice blast resistance, as exhibited in a near-isogenic line containing the same gene. Further, an F1 hybrid obtained by using this rice male sterile line as a seed parent contains the Modan-derived Pb1 gene and therefore exhibits improved resistance to rice blast, as compared to an F1 hybrid obtained by using a Koshihikari male sterile line as a seed parent. For this reason, in an F1 hybrid breeding method, by using the method for producing a rice F1 seed in accordance with the present invention, seeds of a rice F1 hybrid can be produced with higher efficiency of selection, and efficiency of a combinatorial test for rearing an F1 hybrid can be improved.

A rice male sterile line containing the *O. nivara*-derived Cr1 gene exhibits a high stigma exsertion rate, as exhibited in a near-isogenic line containing the same gene. Further, an F1 hybrid obtained by using this rice male sterile line as a seed parent contains the *O. nivara*-derived Cr1 gene and therefore exhibits an improved stigma exsertion rate, as compared to an F1 hybrid obtained by using a Koshihikari male sterile line as a seed parent. For this reason, in an F1 hybrid breeding method, by using the method for producing a rice F1 seed in accordance with the present invention, an opportunity of the rice male sterile line to receive pollen is increased, and seeds of a rice F1 hybrid can be obtained with higher seed production efficiency.

Other chromosome fragments derived from a foreign cultivar may be introduced into the rice male sterile line used in the present invention in addition to the Pb1 gene derived from *Oryza sativa* L. cultivar Modan or the Cr1 gene derived from *Oryza nivara*. For example, as disclosed in Patent Document 3 or Patent Document 4, an sd1 gene derived from *Oryza sativa* L. cultivar Habataki, an hd1 gene derived from *Oryza sativa* L. cultivar Habataki, and a Gn1 gene derived from *Oryza sativa* L. cultivar Habataki may be introduced into the rice male sterile line of the present invention. A rice male sterile line into which these genes have been additionally introduced may be obtained by crossing a near-isogenic line where at least one of these genes has been introduced into a chromosome of *Oryza sativa* L. cultivar Koshihikari, with Modan-derived Pb1-containing rice near-isogenic line, *O. nivara*-derived Cr1-containing near-isogenic line, or Modan-derived Pb1/*O. nivara*-derived Cr1-containing near-isogenic line, and selecting an individual where a gene derived from the foreign gene introduced into a chromosome of *Oryza sativa* L. cultivar Koshihikari has been introduced into homologous chromosomes of both parties, using a DNA marker, from the F2 hybrid obtained by self-mating the resulting F1 hybrid.

A near-isogenic line of *Oryza sativa* L. cultivar Koshihikari where a region in which the sd1 gene in a chromosome of *Oryza sativa* L. cultivar Koshihikari is encoded has been substituted with a chromosome fragment containing a region encoding the sd1 gene derived from *Oryza sativa* L. cultivar Habataki (Habataki-derived sd1-containing near-isogenic line), a near-isogenic line of *Oryza sativa* L. cultivar Koshihikari where a region in which the Gn1 gene in a chromosome of *Oryza sativa* L. cultivar Koshihikari is encoded has been substituted with a chromosome fragment containing a region encoding the Gn1 gene derived from *Oryza sativa* L. cultivar Habataki (Habataki-derived Gn1-containing near-isogenic line), and a near-isogenic line of *Oryza sativa* L. cultivar Koshihikari where a region in which the hd1 gene in a chromosome of *Oryza sativa* L. cultivar Koshihikari is encoded has been substituted with a chromosome fragment containing a region encoding the hd1 gene derived from *Oryza sativa* L. cultivar Habataki (Habataki-derived hd1-containing near-isogenic line) may be created, for example, by using an appropriate DNA marker, according to the method disclosed in Patent Document 3 and Patent Document 4 or other methods. Further, a near-isogenic line where two or more genes of these genes have been substituted for Habataki-derived genes may be obtained by crossing near-isogenic lines where different kinds of genes have been substituted for Habataki-derived genes, and selecting a homo-individual where a gene derived from the foreign gene introduced into a chromosome of *Oryza sativa* L. cultivar Koshihikari has been introduced into homologous chromosomes of both parties, using a DNA marker, from the F2 hybrid obtained by self-mating the resulting F1 hybrid.

Figure 3:
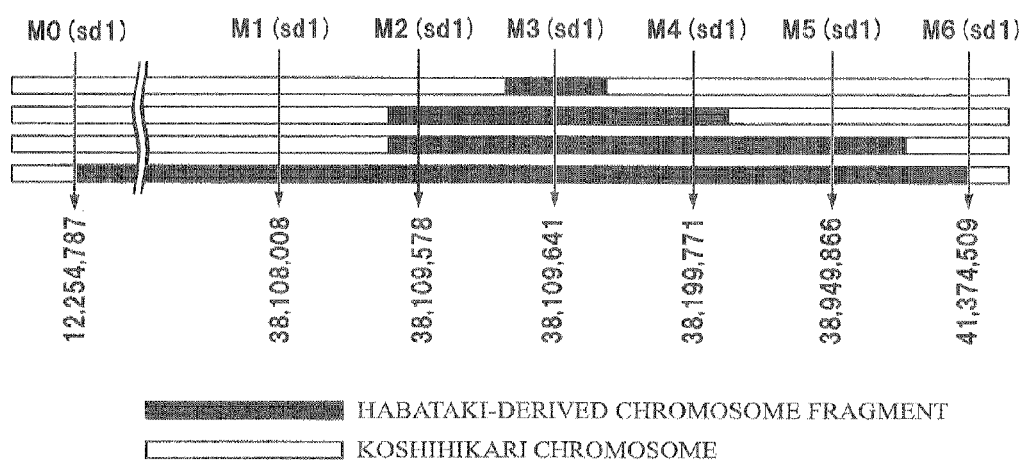
FIG. 3 is a view showing a DNA marker (SNP) of the vicinity in which the sd1 gene in the chromosome 1 of rice is encoded.

The Habataki-derived chromosome fragment contained in the Habataki-derived sd1-containing near-isogenic line is not particularly limited as long as it contains a region in which the sd1 gene is encoded, and may contain only the region in which the sd1 gene is encoded, and a gene present in the proximity of the sd1 gene, together with the sd1 gene, may also be inserted into *Oryza saliva* L. cultivar Koshihikari. FIG. 3 shows a DNA marker (SNP) of approximately 38.11 Mbp in which the sd1 gene in the chromosome 1 of rice is encoded. A length of the Habataki-derived chromosome fragment may be determined by using a DNA marker. For example, as shown in FIG. 3, in the Habataki-derived sd1-containing near-isogenic line, an end on an upstream side of the inserted Habataki-derived chromosome fragment may be present between polymorphism dependent on the base sequence at the position of 38,109,578 in the chromosome 1 of *Oryza sativa* L. cultivar Nipponbare (when performing PCR, the PCR product can be obtained from *Oryza sativa* L. cultivar Koshihikari, whereas the PCR product cannot be obtained from *Oryza sativa* L. cultivar Habataki) (hereinafter, referred to as "G2003") and polymorphism dependent on the base sequence at the position of 38,109,641 in the chromosome 1 of *Oryza sativa* L. cultivar Nipponbare (when performing PCR, the PCR product can be obtained from *Oryza sativa* L. cultivar Koshihikari, whereas the PCR product cannot be obtained from *Oryza sativa* L. cultivar Habataki) (hereinafter, referred to as "G2002"), and an end on a downstream side of the Habataki-derived chromosome fragment may be present between G2003 and SNP corresponding to SNP at the position of 38,199,771 in the chromosome 1 of *Oryza sativa* L. cultivar Nipponbare (G in *Oryza sativa* L. cultivar Koshihikari, and T in *Oryza sativa* L. cultivar Habataki) (hereinafter, referred to as "SP-462") (first step in FIG. 3). Alternatively, an end on an upstream side of the Habataki-derived chromosome fragment may be present between SNP corresponding to SNP at the position of 38,108,008 in the chromosome 1 of *Oryza saliva* L. cultivar Nipponbare (G in *Oryza sativa* L. cultivar Koshihikari, and C in *Oryza saliva* L. cultivar Habataki) (hereinafter, referred to as "SP-4009") and G2003, and an end on a downstream side of the Habataki-derived chromosome fragment may be present between SP-462 and SNP corresponding to SNP at the position of 38,949,866 in the chromosome 1 of *Oryza sativa* L. cultivar Nipponbare (T in *Oryza sativa* L. cultivar Koshihikari, and C in *Oryza sativa* L. cultivar Habataki) (hereinafter, referred to as "SP-1259") (second step in FIG. 3). An end on an upstream side of the Habataki-derived chromosome fragment may be present between SP-4009 and G2003, and an end on a downstream side of the Habataki-derived chromosome fragment may be present between SP-1259 and SNP corresponding to SNP at the position of 41,374,509 in the chromosome 1 of *Oryza sativa* L. cultivar Nipponbare (A in *Oryza sativa* L. cultivar Koshihikari, and G in *Oryza sativa* L. cultivar Habataki) (hereinafter, referred to as "SP-477") (third step in FIG. 3). Further, a longer region, containing a region encoding the sd1 gene derived from *Oryza sativa* L. cultivar Habataki, may be substituted with the Habataki-derived chromosome fragment. For example, the region containing a region of approximately 29.1 Mbp ranging from SNP corresponding to SNP at the position of 12,254,787 in the chromosome 1 of *Oryza sativa* L. cultivar Nipponbare (G in *Oryza sativa* L. cultivar Koshihikari, and C in *Oryza sativa* L. cultivar Habataki) (hereinafter, referred to as "SP-2058") to SP-477 may be substituted with the Habataki-derived chromosome fragment (fourth step in FIG. 3). Base sequences of individual DNA markers and primers usable in discrimination are shown in Table 3.

Koshihikari male sterile line as a seed parent. For this reason, in the method for producing a rice F1 seed in accordance with the present invention, by using a rice male sterile line containing the Habataki-derived sd1 gene, seeds of an F1 hybrid with improved lodging resistance can be efficiently produced, and efficiency of a combinatorial test for rearing an F1 hybrid can be improved.

Figure 4:
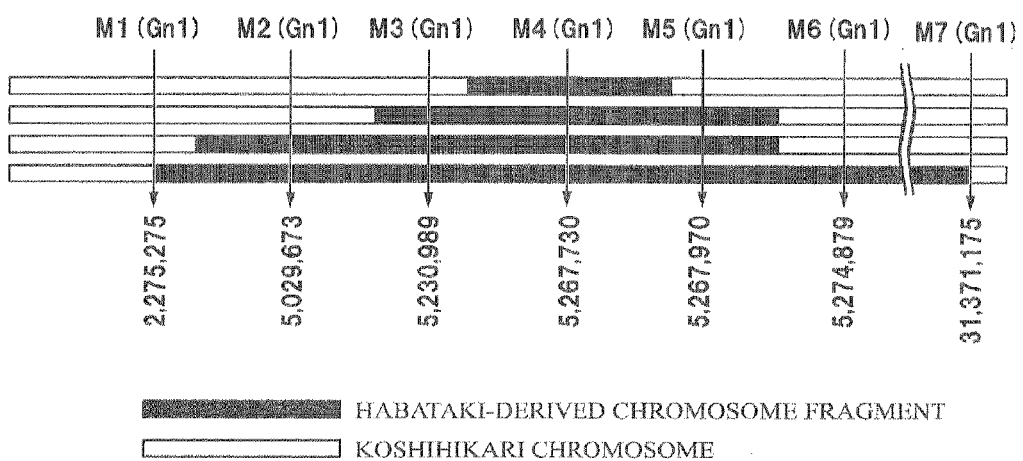
FIG. 4 is a view showing a DNA marker (SNP) of the vicinity in which the Gn1 gene in the chromosome 1 of rice is encoded.

The Habataki-derived chromosome fragment contained in the Habataki-derived Gn1-containing near-isogenic line is not particularly limited as long as it contains a region in which the Gn1 gene is encoded, and may contain only the region in which the Gn1 gene is encoded, and a gene present in the proximity of the Gn1 gene, together with the Gn1 gene, may also be inserted into *Oryza sativa* L. cultivar Koshihikari. FIG. 4 shows a DNA marker (SNP) of approximately 5.267 Mbp in which the Gn1 gene in the chromosome 1 of rice is encoded. A length of the Habataki-derived chromosome fragment may be determined by using a DNA marker. For example, as shown in FIG. 4, in the Habataki-derived Gn1-containing near-isogenic line, an end on an upstream side of the inserted Habataki-derived chromosome fragment may be present between SNP corresponding to SNP at the position of 5,230,989 in the chromosome 1 of *Oryza sativa* L. cultivar Nipponbare (T in *Oryza sativa* L. cultivar Koshihikari, and A in *Oryza sativa* L. cultivar Habataki) (hereinafter, referred to as "SP-170") and SNP corresponding to SNP at the position of 5,267,730 in the chromosome 1 of *Oryza sativa* L. cultivar Nipponbare (A in *Oryza sativa* L. cultivar Koshihikari, and C in *Oryza saliva* L. cultivar Habataki) (hereinafter, referred to as "SP-4028"), and an end on a downstream side of the Habataki-derived chromosome fragment may be present between SP-4028 and SNP corresponding to SNP at the position of 5,267,970 in the chromosome 1 of *Oryza saliva* L. cultivar Nipponbare (G in *Oryza sativa* L. cultivar Koshihikari, and C in *Oryza sativa* L. cultivar Habataki) (hereinaf-

TABLE 3

| | Marker | Position in the chromosome 1 | Type | Sequence | SEQ ID NO: |
|---|---|---|---|---|---|
| M0(sd1) | SP-2058 | 12,254,787 | Gc | Upper Seq: TGCTACAACTGTACACACTG | 37 |
| | | | | Lower Seq: GCTCGAAGACACATTGGTTC | 38 |
| | | | | SNP primer: AGTAGAAAAACCAACACCTT | 39 |
| M1(sd1) | SP-4009 | 38,108,008 | Gc | Upper Seq: CCGTTATGTGCCTGTATGG | 40 |
| | | | | Lower Seq: TGTTGCAGGAAGGTGACAGG | 41 |
| | | | | SNP primer: TTGGAAGGAACATCTAGCACA | 42 |
| M2(sd1) | G2003 | 38,109,578 | PCR | Upper Seq: CACAGCGCTCACTTCTCA | 43 |
| | | | | Lower Seq: TGCAATGTCGTCCACCATCG | 44 |
| M3(sd1) | G2002 | 38,109,641 | PCR | Upper Seq: CACAGCGCTCACTTCTCA | 45 |
| | | | | Lower Seq: ATGATCGTCAGCGACAGCT | 46 |
| M4(sd1) | SP-462 | 38,199,771 | Gt | Upper Seq: AACTCCAGCGTGCTAAGC | 47 |
| | | | | Lower Seq: GCATTGCATGCAGGATCG | 48 |
| | | | | SNP primer: AGAGCCCTTCACTTTCAGC | 49 |
| M5(sd1) | SP-1259 | 38,949,866 | Tc | Upper Seq: AAGGCTGATGAGCACTGC | 50 |
| | | | | Lower Seq: GGCATTGTGGAAGCTCTTC | 51 |
| | | | | SNP primer: TCTCCTTTCGGAGTCCC | 52 |
| M6(sd1) | SP-477 | 41,374,509 | Ag | Upper Seq: GCTATGTTGAACAAGTTCGCTG | 53 |
| | | | | Lower Seq: CATCGTGGACAGCAATCTTG | 54 |
| | | | | SNP primer: GTATAGTTAGTCATGTGCC | 55 |

An F1 hybrid obtained by using the rice male sterile line containing the Habataki-derived sd1 gene as a seed parent contains the Habataki-derived sd1 gene and therefore exhibits a significantly low culm length and improved lodging resistance, as compared to an F1 hybrid obtained by using a ter, referred to as "SP-4038") (first step in FIG. 4). Alternatively, an end on an upstream side of the Habataki-derived chromosome fragment may be present between SNP corresponding to SNP at the position of 5,029,673 in the chromosome 1 of *Oryza sativa* L. cultivar Nipponbare (T in *Oryza* sativa L. cultivar Koshihikari, and G in *Oryza sativa* L. cultivar Habataki) (hereinafter, referred to as "SP-2032") and SP-170, and an end on a downstream side of the Habataki-derived chromosome fragment may be present between SP-4038 and SNP corresponding to SNP at the position of 5,274,879 in the chromosome 1 of *Oryza sativa* L. cultivar Nipponbare (A in *Oryza saliva* L. cultivar Koshihikari, and T in *Oryza saliva* L. cultivar Habataki) (hereinafter, referred to as "SP-4030") (second step in FIG. 4). An end on an upstream side of the Habataki-derived chromosome fragment may be present between SNP corresponding to SNP at the position of 2,275,275 in the chromosome 1 of *Oryza sativa* L. cultivar Nipponbare (G in *Oryza sativa* L. cultivar Koshihikari, and C in *Oryza sativa* L. cultivar Habataki) (hereinafter, referred to as "SP-158") and SP-2032, and an end on a downstream side of the Habataki-derived chromosome fragment may be present between SP-4038 and SP-4030 (third step in FIG. 4). Further, a longer region, containing a region encoding the Gn1 gene derived from *Oryza sativa* L. cultivar Habataki may be substituted with the Habataki-derived chromosome fragment. For example, the region containing a region of approximately 29.1 Mbp ranging from SP-158 to SNP corresponding to SNP at the position of 31,371,175 in the chromosome 1 of *Oryza sativa* L. cultivar Nipponbare (G in *Oryza sativa* L. cultivar Koshihikari, and A in *Oryza sativa* L. cultivar Habataki) (hereinafter, referred to as "SP-262") may be substituted with the Habataki-derived chromosome fragment (fourth step in FIG. 4). Base sequences of individual DNA markers and primers usable in discrimination are shown in Table 4.

male sterile line containing the Habataki-derived Gn1 gene, seeds of an F1 hybrid with improved grain density can be efficiently produced, and efficiency of a combinatorial test for rearing an F1 hybrid can be improved.

Figure 5:
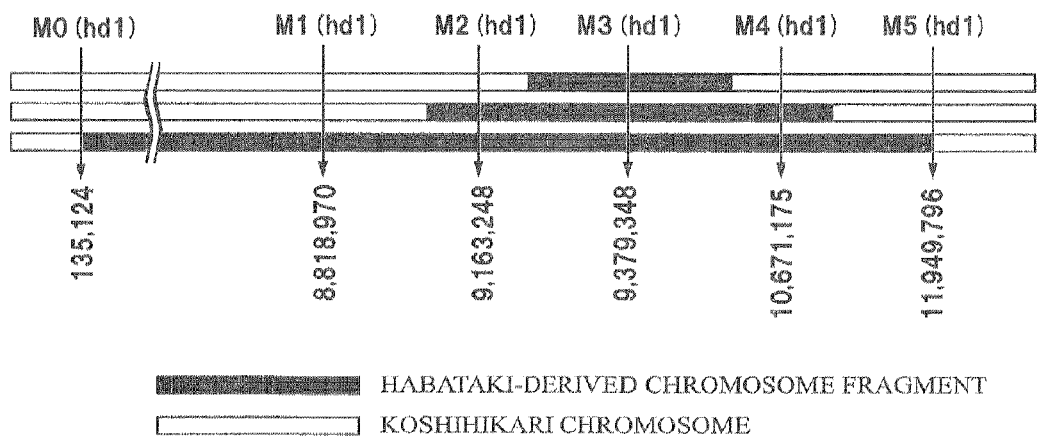
FIG. 5 is a view showing a DNA marker (SNP) of the vicinity in which the hd1 gene in the chromosome 6 of rice is encoded.

The Habataki-derived chromosome fragment contained in the Habataki-derived hd1-containing near-isogenic line is not particularly limited as long as it contains a region in which the hd1 gene is encoded, and may contain only the region in which the hd1 gene is encoded, and a gene present in the proximity of the hd1 gene, together with the hd1 gene, may also be inserted into *Oryza sativa* L. cultivar Koshihikari. FIG. 5 shows a DNA marker (SNP) of approximately 9.38 Mbp in which the hd1 gene in the chromosome 1 of rice is encoded. A length of the Habataki-derived chromosome fragment may be determined by using a DNA marker. For example, as shown in FIG. 5, in the Habataki-derived hd1-containing near-isogenic line, an end on an upstream side of the inserted Habataki-derived chromosome fragment may be present between SNP corresponding to SNP at the position of 9,163,248 in the chromosome 6 of *Oryza saliva* L. cultivar Nipponbare (C in *Oryza sativa* L. cultivar Koshihikari, and A in *Oryza saliva* L. cultivar Habataki) (hereinafter, referred to as "SP-586") and SNP corresponding to SNP at the position of 9,379,348 in the chromosome 6 of *Oryza sativa* L. cultivar Nipponbare (C in *Oryza sativa* L. cultivar Koshihikari, and G in *Oryza sativa* L. cultivar Habataki) (hereinafter, referred to as "SP-2254"), and an end on a downstream side of the

TABLE 4

| | Marker | Position in the chromosome 1 | Type | Sequence | SEQ ID NO: |
|---|---|---|---|---|---|
| M1(Gn1) | SP-156 | 2,275,275 | Gc | Upper Seq: GGAATTCAGAGACAACATGG | 56 |
| | | | | Lower Seq: GCTTCAGTGTTGTGTGATTCTG | 57 |
| | | | | SNP primer: AACGAGTTCTACAATGCTGC | 58 |
| M2(Gn1) | SP-2032 | 5,029,673 | Tg | Upper Seq: CATTGAGTCCATTTCCTCTGC | 59 |
| | | | | Lower Seq: GCAGCTCCAAGAATGACTAC | 60 |
| | | | | SNP primer: ATTGGTGCTAGAGCAACTAC | 61 |
| M3(Gn1) | SP-170 | 5,230,989 | Ta | Upper Seq: GTGAGACATAGACTATCCAC | 62 |
| | | | | Lower Seq: ACGCGTACGCCACATAGAC | 63 |
| | | | | SNP primer: AGGGTGAGGAATGTCCGGT | 64 |
| M4(Gn1) | SP-4028 | 5,267,730 | Ac | Upper Seq: GCAGTACCTGCCTTACTACG | 65 |
| | | | | Lower Seq: CATTTCATGCGAGTGGTGAC | 66 |
| | | | | SNP primer: TGCACGAATCTTGGCCAGAG | 67 |
| M5(Gn1) | SP-4038 | 5,267,970 | Gc | Upper Seq: CTTAAACTCAACTTGCACAAGTAG | 68 |
| | | | | Lower Seq: ACTGCCGACATGTTACTGTC | 69 |
| | | | | SNP primer: GTCCCACCTGAAACATATCCA | 70 |
| M6(Gn1) | SP-4030 | 5,274,879 | At | Upper Seq: TCTTTGATTCTTTGGTCGATCG | 71 |
| | | | | Lower Seq: GCGTACGAGAGCTATAGAGC | 72 |
| | | | | SNP primer: ATGGATCCGTGGATCGATCG | 73 |
| M7(Gn1) | SP-262 | 31,371,175 | Ga | Upper Seq: GCAGCAGGACAAAGGCTAAC | 74 |
| | | | | Lower Seq: ACCCTTCTTCAAGCTCCATC | 75 |
| | | | | SNP primer: TCACAACCGGACCAGATGAC | 76 |

An F1 hybrid obtained by using the rice male sterile line containing the Habataki-derived Gn1 gene as a seed parent contains the Habataki-derived Gn1 gene and therefore exhibits an improved grain density, as compared to an F1 hybrid obtained by using a Koshihikari male sterile line as a seed parent. For this reason, in the method for producing a rice F1 seed in accordance with the present invention, by using a rice Habataki-derived chromosome fragment may be present between SP-2254 and SNP corresponding to SNP at the position of 10,671,175 in the chromosome 6 of *Oryza sativa* L. cultivar Nipponbare (T in *Oryza sativa* L. cultivar Koshihikari, and C in *Oryza saliva* L. cultivar Habataki) (hereinafter, referred to as "SP-1603") (top in FIG. 5). Further, an end on an upstream side of the Habataki-derived chromosome fragment may be present between SNP corresponding to SNP at the position of 8,818,970 in the chromosome 6 of *Oryza sativa* L. cultivar Nipponbare (C in *Oryza sativa* L. cultivar Koshihikari, and T in *Oryza sativa* L. cultivar Habataki) (hereinafter, referred to as "SP-2513") and SP-586, and an end on a downstream side of the Habataki-derived chromosome fragment may be present between SP-1603 and SNP corresponding to SNP at the position of 11,949,796 in the chromosome 6 of *Oryza sativa* L. cultivar Nipponbare (T in *Oryza sativa* L. cultivar Koshihikari, and C in *Oryza sativa* L. cultivar Habataki) (hereinafter, referred to as "SP-604") (middle in FIG. 5). Further, a longer region, containing a region encoding the hd1 gene derived from *Oryza saliva* L. cultivar Habataki may be substituted with the Habataki-derived chromosome fragment. For example, the region containing a region of approximately 28.9 Mbp ranging from SNP corresponding to SNP at the position of 135,124 in the chromosome 6 of *Oryza sativa* L. cultivar Nipponbare (A in *Oryza sativa* L. cultivar Koshihikari, and G in *Oryza sativa* L. cultivar Habataki) (hereinafter, referred to as "SP-2229") to SNP corresponding to SNP at the position of 29,016,207 in the chromosome 6 of *Oryza sativa* L. cultivar Nipponbare (G in *Oryza sativa* L. cultivar Koshihikari, and T in *Oryza sativa* L. cultivar Habataki) (hereinafter, referred to as "SP-1635") may be substituted with the Habataki-derived chromosome fragment (bottom in FIG. 5). Base sequences of individual DNA markers and primers usable in discrimination are shown in Table 5.

male sterile line containing the Habataki-derived hd1 gene, seeds of an F1 hybrid for which the heading time could be made earlier can be efficiently produced, and efficiency of a combinatorial test for rearing an F1 hybrid can be improved.

The rice male sterile line used in the present invention may be a line which further exhibits semi-waxiness. The rice male sterile line may be created, specifically, in the following manner. First, a near-isogenic line of *Oryza sativa* L. cultivar Koshihikari exhibiting semi-waxiness is crossed with a Modan-derived Pb1-containing rice near-isogenic line, an *O. nivara*-derived Cr1-containing near-isogenic line, or a Modan-derived Pb1/*O. nivara*-derived Cr1-containing near-isogenic line, and an individual where a chromosome fragment derived from the foreign gene introduced into a chromosome of *Oryza sativa* L. cultivar Koshihikari has been introduced into homologous chromosomes of both parties is selected from the F2 hybrid obtained by self-mating the resulting F1 hybrid, using a DNA marker. Then, the resulting F2 hybrid is self-mated again, and a rice individual exhibiting semi-waxiness in every seed is selected from the resulting F3 hybrid. The thus-obtained rice individual is a near-isogenic line of Koshihikari which exhibits semi-waxiness and also has at least one of Modan-derived Pb1 gene and *O. nivara*-derived Cr1 gene as a homo type. A rice male sterile line exhibiting semi-waxiness used in the present invention may be obtained by crossing the near-isogenic line of Koshihikari with a Koshihikari male sterile line, and subjecting the resulting F1 hybrid to continuous backcrossing using the near-isogenic line of *Oryza sativa* L. cultivar Koshihikari as a pollen parent.

TABLE 5

| Marker | Position in the chromosome 6 | Type | Sequence | SEQ ID NO: |
|---|---|---|---|---|
| M0(hd1) | SP-2229 | 135,124 | Ag | Upper Seq: CAATCTGGGATTCTGGATCAG | 77 |
| | | | | Lower Seq: AGCTCAGTATCACGGACTTG | 78 |
| | | | | SNP primer: GTCTCTTTTAACACACCTTAC | 79 |
| M1(hd1) | SP-2513 | 8,818,970 | Ct | Upper Seq: GCGAAAAGATGAGGATGTACAC | 80 |
| | | | | Lower Seq: CCGTAGGCCTTTGTCAAGTG | 81 |
| | | | | SNP primer: CTTTAATGGTGGCTTATGTC | 82 |
| M2(hd1) | SP-586 | 9,163,248 | Ca | Upper Seq: GCTAGGACAAGCTTATTTCAGC | 83 |
| | | | | Lower Seq: TCACGCCGATCAAGAACG | 84 |
| | | | | SNP primer: CATAATTTATCGCCATTTTCGCAT | 85 |
| M3(hd1) | SP-2254 | 9,379,348 | Cg | Upper Seq: AGGCCCTTGTACTGGTAC | 86 |
| | | | | Lower Seq: GTACACAATAGTTGGTGCACC | 87 |
| | | | | SNP primer: CATGATAAGGTACTCCTGG | 88 |
| M4(hd1) | SP-1603 | 10,671,175 | Tc | Upper Seq: CCTAGTCCCTAAAGATCTCATG | 89 |
| | | | | Lower Seq: GATAGACATGACGGAGAAGTG | 90 |
| | | | | SNP primer: GGGTGGTGTTATCTCTAGT | 91 |
| M5(hd1) | SP-604 | 11,949,796 | Tc | Upper Seq: GCGCAAATTCCTTCAGTCAC | 92 |
| | | | | Lower Seq: CAGTTTCAGGTGGAAGACC | 93 |
| | | | | SNP primer: CAAGTTTCTTCCTCTCATTTTC | 94 |
| M6(hd1) | SP-1635 | 29,016,207 | Gt | Upper Seq: TAGGAGTGAATGGCGGTAAG | 95 |
| | | | | Lower Seq: GTATATCCCGACAATAGTCCTG | 96 |
| | | | | SNP primer: GTACATGATAATACAGCAAAGATT | 97 |

An F1 hybrid obtained by using the rice male sterile line containing the Habataki-derived hd1 gene as a seed parent contains the Habataki-derived hd1 gene and therefore becomes an early season cultivar, as compared to an F1 hybrid obtained by using a Koshihikari male sterile line as a seed parent. For this reason, in the method for producing a rice F1 seed in accordance with the present invention, by using a rice The near-isogenic line of *Oryza sativa* L. cultivar Koshihikari exhibiting semi-waxiness may be obtained, for example, from a mutant group of *Oryza sativa* L. cultivar Koshihikari by the selection depending on a phenotypic characteristic expressing semi-waxiness, or a type of a gene contributing to semi-waxiness (semi-waxiness gene) using a DNA marker. The semi-waxiness gene may be, for example, a waxy-mq gene present in the chromosome 6 of *Oryza sativa* L. cultivar. Further, the near-isogenic line of *Oryza sativa* L. cultivar Koshihikari exhibiting semi-waxiness may be a mutant of known *Oryza sativa* L. cultivar Koshihikari such as *Oryza sativa* L. cultivar Milky Queen, which is mutant of a waxy-mq gene, or a near-isogenic line obtained by continuous backcrossing of *Oryza sativa* L. cultivar Koshihikari with semi-waxiness-expressing *Oryza sativa* L. cultivar other than *Oryza sativa* L. cultivar Koshihikari (for example, mutants derived from other cultivar).

EXAMPLES

The present invention will now be described in more detail with reference to Examples, but the present invention is not limited to the following Examples.

Example 1

<Modan-Derived Pb1-Containing Near-Isogenic Line (Pb1-NIL) JMT-019>

According to the method described in Patent Document 3, a Modan-derived Pb1-containing near-isogenic line JMT-019 (hereinafter, also referred to as "JMT-019") was created. More specifically, first, an individual having a desired genome was selected using SP-4234, SP-5290, SP-5384, SP-5569, and SP-4236 among DNA markers described in Table 1.

Figure 6:
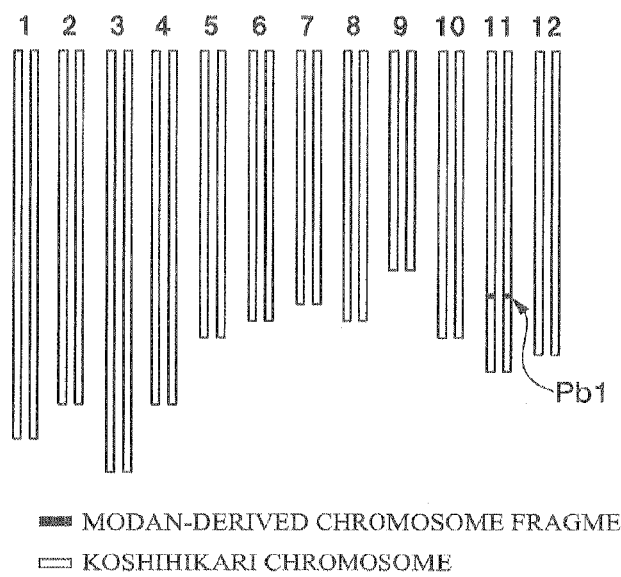
FIG. 6 is a view schematically showing a genome of a Modan-derived Pb1-containing near-isogenic line (Pb1-NIL) JMT-019 created in Example 1.

Specifically, *Oryza sativa* L. cultivar Koshihikari was backcrossed five times with *Oryza sativa* L. cultivar Modan. A seed of the resulting F5 hybrid was further cultivated, and a seedling was grown to such an extent that the seedling could be transplanted to an agricultural field. DNA was extracted from a leaf of each cultivated individual, and one cultivated individual in which SP-4234 and SP-4236 are a homo-chromosome region of an allele derived from Koshihikari, and SP-5290, SP-5384 and SP-5569 are a homo-chromosome region of an allele derived from Modan was selected. This selected cultivated individual is a new cultivar in which the region containing the Pb1 gene was substituted with a Modan-derived chromosome fragment. The present inventors designated this new cultivar as "JMT-019". FIG. 6 schematically shows a genome of a Modan-derived Pb1-containing near-isogenic line (Pb 1-NIL) JMT-019. Further, the relationship between the Modan-derived chromosome fragment-substituted region in the Modan-derived Pb1-containing near-isogenic line (Pb1-NIL) JMT-019 and the DNA markers given in Table 1 is as shown in the middle of FIG. 1.

Characteristics of JMT-019 and Koshihikari were compared and studied. Study of characteristics was carried out according to Property Examination for filing Variety Registration based on The Plant Variety Protection and Seed Act (Act No. 83 of 1998), Article 5(1). As a result, JMT-019 was fundamentally the same as Koshihikari except that resistance to rice blast was high.

<*O. nivara*-Derived Cr1-Containing Near-Isogenic Line (Cr1-NIL) JMT-020>

According to the method described in Patent Document 3, an *O. nivara*-derived Cr1-containing near-isogenic line JMT-020 (hereinafter, also referred to as "JMT-020") was created. More specifically, an individual having a desired genome was selected using SP-4141, SP-3823, SP-3826, and SP-306 among DNA markers described in Table 2.

Figure 7:
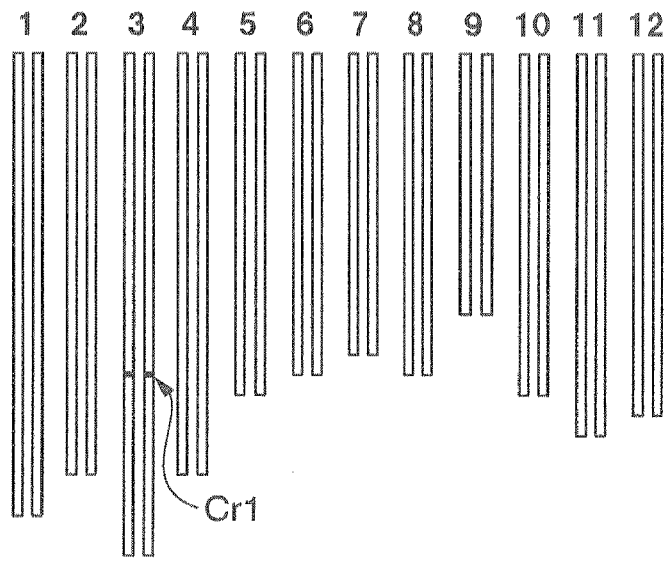
FIG. 7 is a view schematically showing a genome of an *O. nivara*-derived Cr1-containing near-isogenic line (Cr1-NIL) JMT-020 created in Example 1.

Specifically, *Oryza sativa* L. cultivar Koshihikari was backcrossed five times with rice cultivar *O. nivara*. A seed of the resulting F5 hybrid was further cultivated, and a seedling was grown to such an extent that the seedling could be transplanted to an agricultural field. DNA was extracted from a leaf of each cultivated individual, and one cultivated individual in which SP-4141 and SP-306 are a homo-chromosome region of an allele derived from Koshihikari, and SP-3823 and SP-3826 are a homo-chromosome region of an allele derived from *O. nivara* was selected. This selected cultivated individual is a new cultivar in which the region containing the Cr1 gene was substituted with an *O. nivara*-derived chromosome fragment. The present inventors designated this new cultivar as "JMT-020". FIG. 7 schematically shows a genome of an *O. nivara*-derived Cr1-containing near-isogenic line (Cr1-NIL) JMT-020. Further, the relationship between the *O. nivara*-derived chromosome fragment-substituted region in the *O. nivara*-derived Cr1-containing near-isogenic line (Cr1-NIL) JMT-020 and the DNA markers given in Table 2 is as shown in the top of FIG. 2.

In the same manner as in JMT-019, characteristics of JMT-020 and Koshihikari were compared and studied. As a result, JMT-020 was fundamentally the same as Koshihikari except that a stigma exsertion rate was increased by 45 to 128%.

<*O. nivara*-Derived Cr1-Containing Near-Isogenic Line (Cr1-NIL) JMT-020_Long Region>

According to the method described in Patent Document 3, an *O. nivara*-derived Cr1-containing near-isogenic line JMT-020_long region (hereinafter, also referred to as "JMT-020_long region") was created. More specifically, an individual having a desired genome was selected using SP-3819, SP-4141, SP-3823, SP-3826, and SP-306 among DNA markers described in Table 2.

Figure 8:
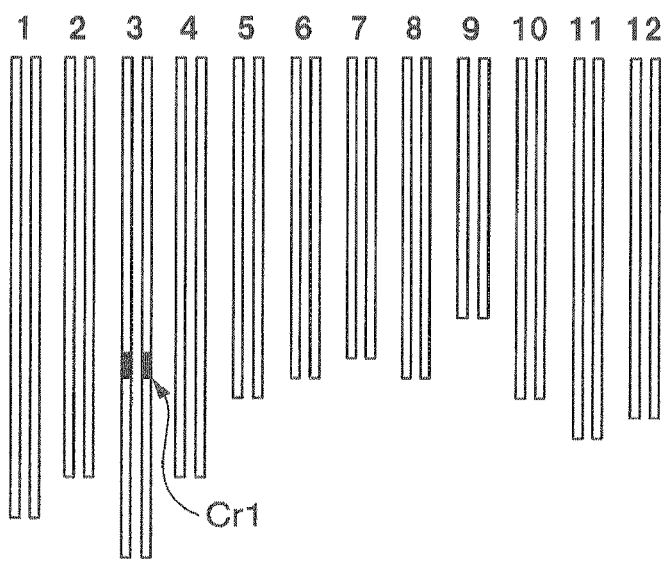
FIG. 8 is a view schematically showing a genome of an *O. nivara*-derived Cr1-containing near-isogenic line (Cr1-NIL) JMT-020_long region created in Example 1.

Specifically, *Oryza sativa* L. cultivar Koshihikari was backcrossed five times with rice cultivar *O. nivara*. A seed of the resulting F5 hybrid was further cultivated, and a seedling was grown to such an extent that the seedling could be transplanted to an agricultural field. DNA was extracted from a leaf of each cultivated individual, and one cultivated individual in which SP-3819 and SP-306 are a homo-chromosome region of an allele derived from Koshihikari, and SP-4141, SP-3823 and SP-3826 are a homo-chromosome region of an allele derived from *O. nivara* was selected. This selected cultivated individual is a new cultivar in which the region containing the Cr1 gene was substituted with an *O. nivara*-derived chromosome fragment. The present inventors designated this new cultivar as "JMT-020_long region". FIG. 8 schematically shows a genome of an *O. nivara*-derived Cr1-containing near-isogenic line (Cr1-NIL) JMT-020_long region. Further, the relationship between the *O. nivara*-derived chromosome fragment-substituted region in the *O. nivara*-derived Cr1-containing near-isogenic line (Cr1-NIL) JMT-020_long region and the DNA markers given in Table 2 is as shown in the middle of FIG. 2.

In the same manner as in JMT-019, characteristics of JMT-020_long region and Koshihikari were compared and studied. As a result, JMT-020_long region was fundamentally the same as Koshihikari except that a stigma exsertion rate was increased by 45 to 128%. In other words, no particular difference was observed in characteristics between JMT-020_long region and JMT-020. From these results, it is inferred that incorporation of a Cr1 gene-encoding region into an *O. nivara*-derived chromosome fragment being introduced into *Oryza sativa* L. cultivar Koshihikari is capable of improving a stigma exsertion rate, and the relative length of the *O. nivara*-derived chromosome fragment has little effect on stigma exsertion rate.

<Modan-Derived Pb1/*O. nivara*-Derived Cr1-Containing Near-Isogenic Line (Pb1/Cr1-NIL)>

JMT-019 and JMT-020_long region were mated, and 2 individuals out of the resulting progeny individuals (seeds)

were cultivated and self-fertilized (self-mated) to further harvest 100 seeds which are progeny individuals. All of these 100 seeds were cultivated, and a DNA marker of each progeny individual was investigated. One cultivated individual in which SP-5384 [M3(Pb1)] is a homo-chromosome region of an allele derived from Modan, and SP-3823 [M3(Cr1)] is a homo-chromosome region of an allele derived from *O. nivara* was selected. This selected cultivated individual is a new cultivar in which the region containing the Pb1 gene was substituted with a Modan-derived chromosome fragment (homo), and the region containing the Cr1 gene was substituted with an *O. nivara*-derived chromosome fragment (homo). The present inventors designated this new cultivar as "JMT-025".

In the same manner as in JMT-019, characteristics of JMT-025 and Koshihikari were compared and studied.

As a result, JMT-025 was fundamentally the same as Koshihikari except that rice blast resistance and a stigma exsertion rate were increased.

<Modan-Derived Pb1/*O. nivara*-Derived Cr1/Habataki-Derived sd1/Habataki-Derived Gn1-Containing Near-Isogenic Line (Pb1/Cr1/sd1/Gn1-NIL)>

Figure 9:
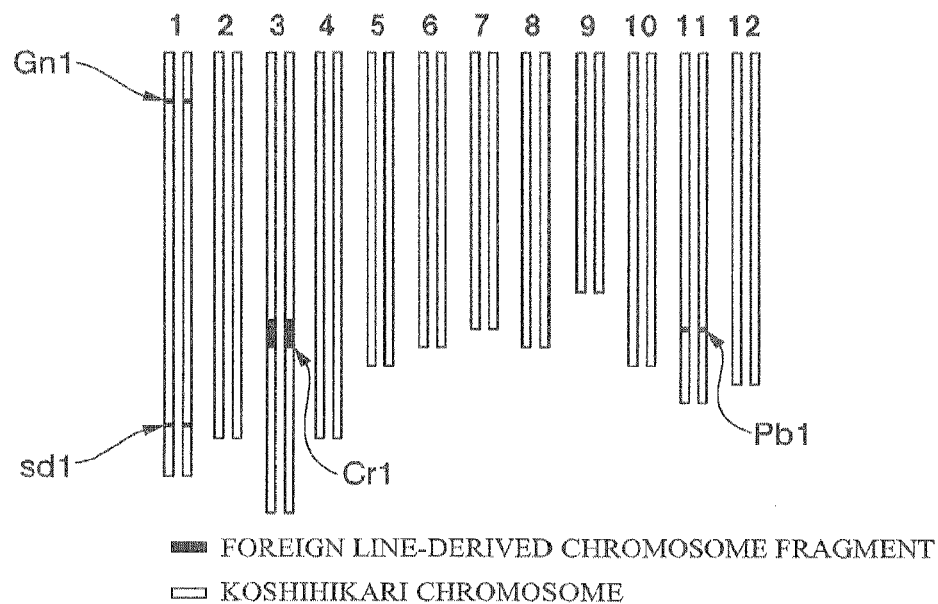
FIG. 9 is a view schematically showing a genome of a Modan-derived Pb1/*O. nivara*-derived Cr1/Habataki-derived sd1/Habataki-derived Gn1-containing near-isogenic line (Pb1/Cr1/sd1/Gn1-NIL) JMT-021 created in Example 1.

JMT-025 and *Oryza sativa* L. cultivar Koshihikari eichi 4go disclosed in Patent Document 4 (a near-isogenic line in which the region containing the sd1 gene of Koshihikari has been substituted with a Habataki-derived chromosome fragment) were mated, and 2 individuals out of the resulting progeny individuals (seeds) were cultivated and self-fertilized (self-mated) to further harvest 100 seeds which are progeny individuals. All of these 100 seeds were cultivated, and a DNA marker of each progeny individual was investigated. One cultivated individual in which all of the region containing the Modan-derived Pb1 gene, the region containing the *O. nivara*-derived Cr1 gene and the region containing the Habataki-derived sd1 gene are a homo-chromosome region of an allele derived from each foreign cultivar was selected. This selected cultivated individual and *Oryza sativa* L. cultivar Koshihikari eichi 2go disclosed in Patent Document 4 (a near-isogenic line in which the region containing the Gn1 gene of Koshihikari has been substituted with a Habataki-derived chromosome fragment) were mated, and 2 individuals out of the resulting progeny individuals (seeds) were cultivated and self-fertilized (self-mated) to further harvest 100 seeds which are progeny individuals. All of these 100 seeds were cultivated, and a DNA marker of each progeny individual was investigated. One cultivated individual in which all of the region containing the Modan-derived Pb1 gene, the region containing the *O. nivara*-derived Cr1 gene, the region containing the Habataki-derived sd1 gene, and the region containing the Habataki-derived Gn1 gene are a homo-chromosome region of an allele derived from each foreign cultivar was selected. This selected cultivated individual is a new cultivar in which the region containing the Pb1 gene was substituted with a Modan-derived chromosome fragment (homo), the region containing the Cr1 gene was substituted with an *O. nivara*-derived chromosome fragment (homo), the region containing the sd1 gene was substituted with a Habataki-derived chromosome fragment (homo), and the region containing the Gn1 gene was substituted with a Habataki-derived chromosome fragment (homo). The present inventors designated this new cultivar as "JMT-021". FIG. 9 schematically shows a genome of (Pb1/Cr1/sd1/Gn1-NIL) JMT-021.

In the same manner as in JMT-019, characteristics of JMT-021 and Koshihikari were compared and studied.

As a result, JMT-021 was fundamentally the same as Koshihikari except that rice blast resistance and a stigma exsertion rate were increased, a culm length was short, lodging resistance was increased, and a grain density was increased.

<Modan-Derived Pb1/*O. Nivara*-Derived Cr1/Habataki-Derived sd1/Habataki-Derived Gn1/Habataki-Derived hd1-Containing Near-Isogenic Line (Pb1/Cr1/sd1/Gn1/hd1-NIL)>

Figure 10:
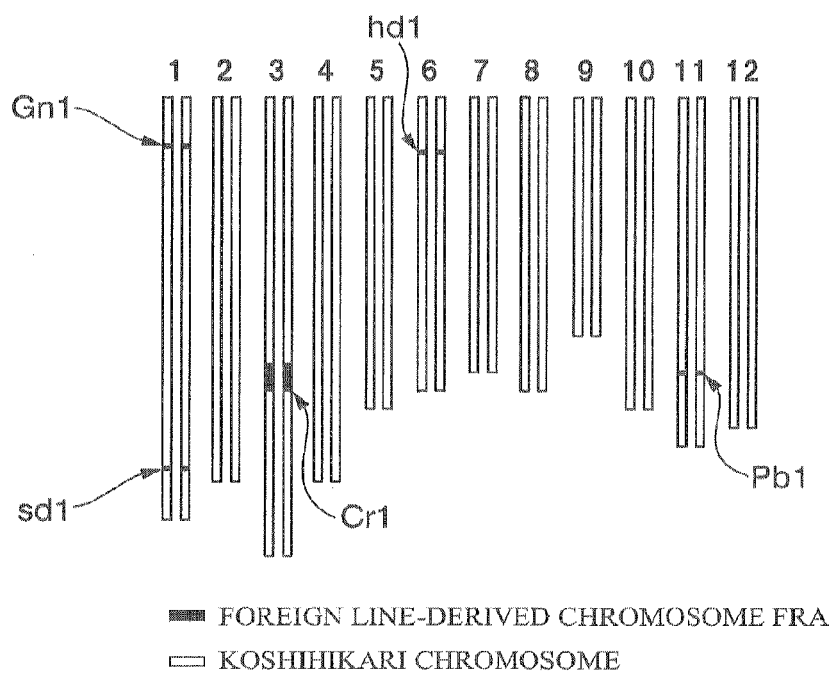
FIG. 10 is a view schematically showing a genome of a Modan-derived Pb1/*O. nivara*-derived Cr1/Habataki-derived sd1/Habataki-derived Gn1/Habataki-derived hd1-containing near-isogenic line (Pb1/Cr1/sd1/Gn1/hd1-NIL) JMT-022 created in Example 1.

JMT-021 and *Oryza sativa* L. cultivar Koshihikari eichi 3go disclosed in Patent Document 4 (a near-isogenic line in which the region containing the hd1 gene of Koshihikari has been substituted with a Habataki-derived chromosome fragment) were mated, and 2 individuals out of the resulting progeny individuals (seeds) were cultivated and self-fertilized (self-mated) to further harvest 100 seeds which are progeny individuals. All of these 100 seeds were cultivated, and a DNA marker of each progeny individual was investigated. One cultivated individual in which all of the region containing the Modan-derived Pb1 gene, the region containing the *O. nivara*-derived Cr1 gene and the region containing the Habataki-derived sd1 gene, Habataki-derived Gn1 gene and Habataki-derived hd1 gene are a homo-chromosome region of an allele derived from each foreign cultivar was selected. This selected cultivated individual is a new cultivar in which the region containing the Pb1 gene was substituted with a Modan-derived chromosome fragment, the region containing the Cr1 gene was substituted with an *O. nivara*-derived chromosome fragment, the region containing the sd1 gene was substituted with a Habataki-derived chromosome fragment, the region containing the Gn1 gene was substituted with a Habataki-derived chromosome fragment, and the region containing the hd1 gene was substituted with a Habataki-derived chromosome fragment. The present inventors designated this new cultivar as "JMT-022". FIG. 10 schematically shows a genome of Pb1/Cr1/sd1/Gn1/hd1-NIL.

In the same manner as in JMT-019, characteristics of JMT-022 and Koshihikari were compared and studied.

As a result, JMT-022 was fundamentally the same as Koshihikari except that rice blast resistance and a stigma exsertion rate were increased, a culm length was short, lodging resistance was increased, a grain density was increased, and conversion into an early season cultivar was achieved.

<Pb1/Cr1/sd1/Gn1-NIL Having Semi-Waxiness>

Figure 11:
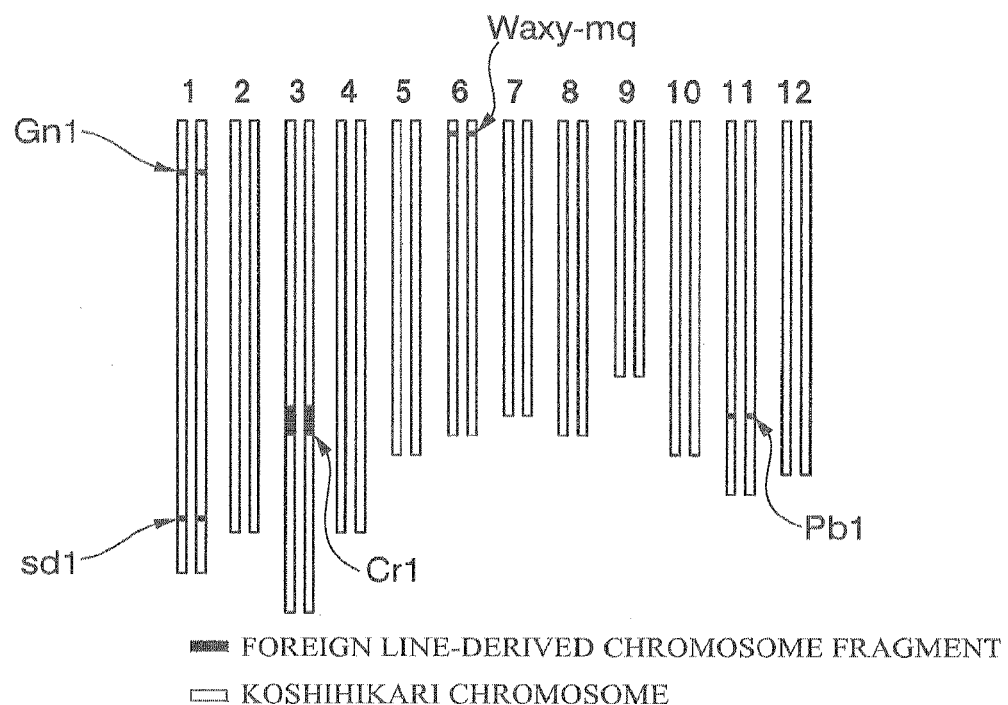
FIG. 11 is a view schematically showing a genome of JMT-023, which is Pb1/Cr1/sd1/Gn1-NIL having semi-waxiness, created in Example 1.

With regard to *Oryza sativa* L. cultivar Milky Queen, which is a semi-waxiness mutant of Koshihikari, JMT-021 was backcrossed five times. A seed of the resulting F5 hybrid was further cultivated, and a cultivated individual exhibiting a brown rice characteristic of semi-waxiness was selected. DNA was extracted from a leaf of each selected cultivated individual, and the DNA marker was investigated, thus confirming that all of the region containing the Modan-derived Pb1 gene, the region containing the *O. nivara*-derived Cr1 gene, the region containing the Habataki-derived sd1 gene, and the region containing the Habataki-derived Gn1 gene are a homo-chromosome region of an allele derived from each foreign cultivar. This selected cultivated individual is a new cultivar in which the region containing the Pb1 gene was substituted with a Modan-derived chromosome fragment, the region containing the Cr1 gene was substituted with an *O. nivara*-derived chromosome fragment, the region containing the sd1 gene was substituted with a Habataki-derived chromosome fragment and the region containing the Gn1 gene was substituted with a Habataki-derived chromosome fragment and which exhibits semi-waxiness. The present inventors designated this new cultivar as "JMT-023". FIG. 11 schematically shows a genome of JMT-023 which is Pb1/Cr1/sd1/Gn1-NIL having semi-waxiness.

In the same manner as in JMT-019, characteristics of JMT-023 and Koshihikari were compared and studied.

As a result, JMT-023 was fundamentally the same as Koshihikari except that rice blast resistance and a stigma exsertion rate were increased, a culm length was short, lodging resistance was increased, a grain density was increased, and semi-waxiness was expressed.

<Pb1/Cr1/sd1/Gn1/hd1-NIL Having Semi-Waxiness>

Figure 12:
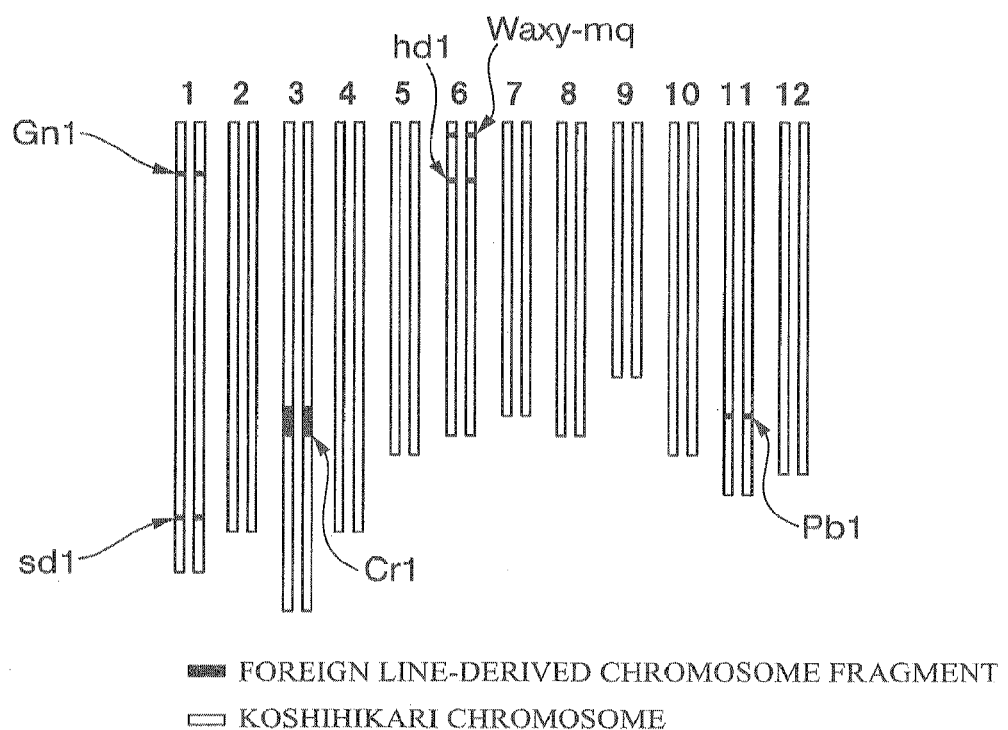
FIG. 12 is a view schematically showing a genome of JMT-023, which is Pb1/Cr1/sd1/Gn1/hd1-NIL having semi-waxiness, created in Example 1.

With regard to Oryza sativa L. cultivar Milky Queen, which is a semi-waxiness mutant of Koshihikari, JMT-022 was backcrossed five times. A seed of the resulting F5 hybrid was further cultivated, and a cultivated individual exhibiting a brown rice characteristic of semi-waxiness was selected. DNA was extracted from a leaf of each cultivated individual selected, and the DNA marker was investigated, thus confirming that all of the region containing the Modan-derived Pb1 gene, the region containing the O. nivara-derived Cr1 gene, the region containing the Habataki-derived sd1 gene, the region containing the Habataki-derived Gn1 gene, and the region containing the Habataki-derived hd1 gene are a homo-chromosome region of an allele derived from each foreign cultivar. This selected cultivated individual is a new cultivar in which the region containing the Pb1 gene was substituted with a Modan-derived chromosome fragment, the region containing the Cr1 gene was substituted with an O. nivara-derived chromosome fragment, the region containing the sd1 gene was substituted with a Habataki-derived chromosome fragment, the region containing the Gn1 gene was substituted with a Habataki-derived chromosome fragment and the region containing the hd1 gene was substituted with a Habataki-derived chromosome fragment and which exhibits semi-waxiness. The present inventors designated this new cultivar as "JMT-024". FIG. 12 schematically shows a genome of JMT-024 which is Pb1/Cr1/sd1/Gn1/hd1-NIL having semi-waxiness.

In the same manner as in JMT-019, characteristics of JMT-024 and Koshihikari were compared and studied.

As a result, JMT-024 was fundamentally the same as Koshihikari except that rice blast resistance and a stigma exsertion rate were increased, a culm length was short, lodging resistance was increased, a grain density was increased, conversion into an early season cultivar was achieved, and semi-waxiness was expressed.

<Cytoplasmic Male Sterile Line of Oryza sativa L. Cultivar Koshihikari (CMS-Koshihikari)>

Oryza sativa L. cultivar Koshihikari was backcrossed 6 times with Oryza sativa L. cultivar CHINSURAH BORO 2, CMS-Koshihikari exhibiting the same characteristic equivalent to Koshihikari except that a growth property in an agricultural field is male sterility was reared.

<Rice Cytoplasmic Male Sterile Line (CMS Line)>

Continuous backcrossing was carried out using CMS-Koshihikari as a seed parent and using JMT-019, JMT-020, JMT-020_long region, JMT-021, JMT-022, JMT-023, or JMT-024 as a pollen parent. Among the resulting progeny individuals, a cultivated individual exhibiting male sterility was selected. DNA was extracted from a leaf of each selected cultivated individual, and a DNA marker was investigated. Each one of cultivated individuals in which the same region as a pollen parent is a homo-chromosome region of an allele derived from a foreign cultivar was selected. Further, with regard to progeny individuals obtained by using JMT-023 or JMT-024 as a pollen parent, first, an individual having semi-waxiness was selected by the naked eye, and a DNA marker of the selected individual was investigated. These selected cultivated individuals are a new cultivar having fundamentally the same characteristic as the pollen parent, except that they are of male sterility. The present inventors designated the rice cytoplasmic male sterile line obtained by using JMT-019 as a pollen parent as "JMS-019", the rice cytoplasmic male sterile line obtained by using JMT-020 as a pollen parent as "JMS-020", the rice cytoplasmic male sterile line obtained by using JMT-020_long region as a pollen parent as "JMS-020_long region", the rice cytoplasmic male sterile line obtained by using JMT-021 as a pollen parent as a "JMS-021", the rice cytoplasmic male sterile line obtained by using JMT-022 as a pollen parent as "JMS-022", the rice cytoplasmic male sterile line obtained by using JMT-023 as a pollen parent as "JMS-023", and the rice cytoplasmic male sterile line obtained by using JMT-024 as a pollen parent as "JMS-024".

Further, from new cultivars obtained in Example 1, the present applicant has deposited JMS-021, JMS-022, JMS-023, JMS-024, JMT-021, JMT-022, JMT-023, and JMT-024 as a novel plant in International Patent Organism Depositary, National Institute of Advanced Industrial Science and Technology (Tsukuba Center Chuou 6th, Higashi 1-1-1, Tsukuba-shi, Ibaraki-ken, Japan).

<Production of F1 Seed>

Each of the above-obtained rice cytoplasmic male sterile lines (CMS line) as a seed parent, and an independently reared restorer line JFR-004 as a pollen parent were mated to harvest a seed of F1 hybrid. As a control, a seed of F1 hybrid was harvested by mating CMS-Koshihikari as a seed parent and JFR-004 as a pollen parent. The F1 seeds thus obtained were cultivated and subjected to study of characteristic in a field test implemented in Aichi Prefecture in 2010. Study of characteristics was carried out according to Property Examination for filing Variety Registration based on The Plant Variety Protection and Seed Act (Act No. 83 of 1998), Article 5(1).

<Rice Blast Resistance Test>

Figure 13:
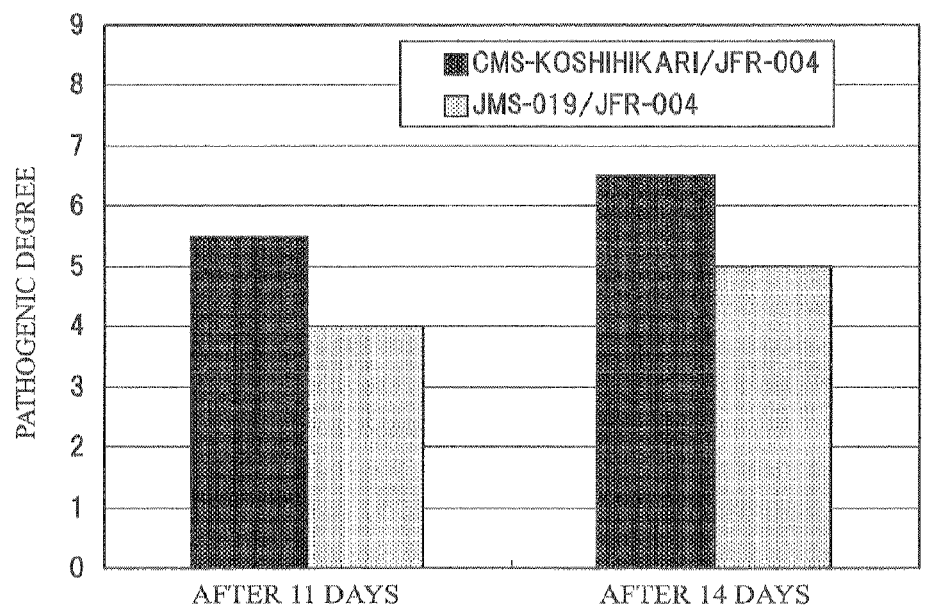
FIG. 13 is a view showing the test results of rice blast resistance performed in Example 1 for an F1 hybrid line (JMS-019/JFR-004) obtained using JMS-019 as a seed parent and for an F1 hybrid line (CMS-Koshihikari/JFR-004) obtained using CMS-Koshihikari as a seed parent.

For the F1 hybrid line (JMS-019/JFR-004) obtained by using JMS-019 as a seed parent and the F1 hybrid line (CMS-Koshihikari/JFR-004) obtained by using CMS-Koshihikari as a seed parent, study of rice blast resistance was carried out in a test field. The test of rice blast resistance was carried out according to "6. How to use rice blast resistance-cold region/natural conditions (epidemic area)_6.1 Test under natural conditions (epidemic area)" described in Rice Breeding Manual (published by Yokendo Co., Ltd., Japan), page 11. Specifically, the present rice line was cultivated in an epidemic area of rice blast in Toyota city, Aichi Prefecture, Japan, and the pathogenic incidence (damage score) of rice blast was investigated 11 days and 14 days after ear emergence. The damage score was evaluated on a 1-10 scale (1: lowest, and 10: highest). The results are given in FIG. 13.

As a result, the damage score after 11 days of ear emergence was 5.5 for the control cultivar, CMS-Koshihikari/JFR-004, whereas JMS-019/JFR-004 exhibited a very low damage score of 4.0. The same tendency was also observed for the damage score after 14 days of ear emergence. In other words, the rice blast resistance was improved more in the F1 hybrid line obtained using JMS-019 as a seed parent, than in the F1 hybrid line obtained using CMS-Koshihikari as a seed parent. From these results, it is clear that when a rice cytoplasmic male sterile line of Oryza sativa L. cultivar Koshihikari into which the Pb1 gene derived from Oryza saliva L. cultivar Modan has been introduced is used as a seed parent, an F1 hybrid with higher rice blast resistance can be created, as compared to when a rice cytoplasmic male sterile line of Oryza sativa L. cultivar Koshihikari is used as a seed parent.

<Measurement of Stigma Exsertion Rate>

Figure 14:
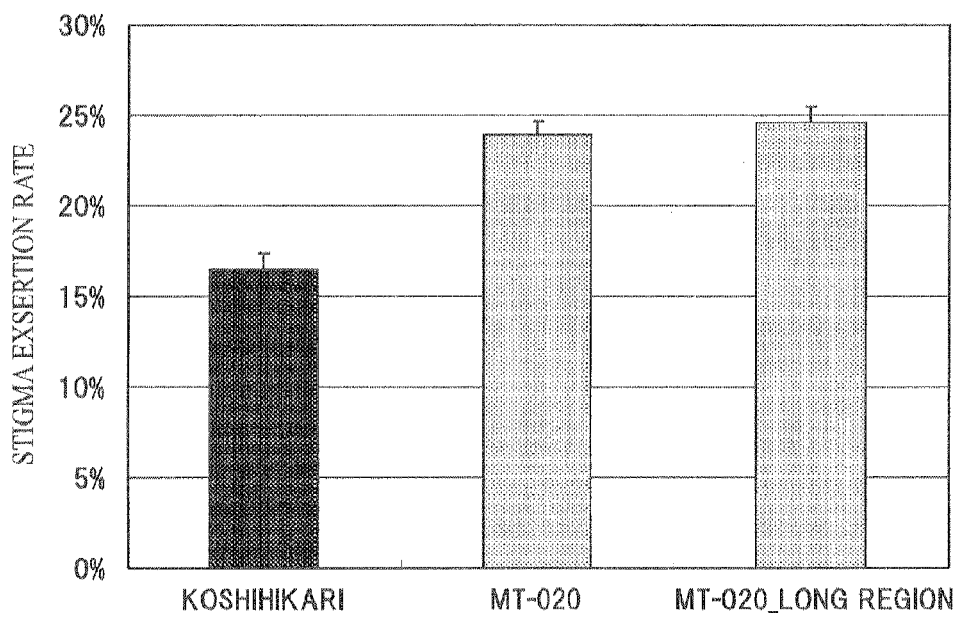
FIG. 14 is a view showing the results of a stigma exsertion rate measured after 7 days from ear emergence of a maintainer line JMT-020, JMT-020_long region, and *Oryza sativa* L. cultivar Koshihikari, in Example 1.

First, JMT-020, JMT-020_long region, and Oryza saliva L. cultivar Koshihikari, which are maintainer lines of the rice cytoplasmic male sterile line in accordance with the present invention, were cultivated in an agricultural field, and ears of rice were sampled after 7 days of ear emergence, followed by measurement of a stigma exsertion rate (fraction of stigma exposed to the outside after fall of flower). The measurement results are shown in FIG. 14. As a result, *Oryza sativa* L. cultivar Koshihikari, which is a control cultivar, exhibited a stigma exsertion rate of about 17%, whereas JMT-020 and JMT-020_long region exhibited a stigma exsertion rate of about 24%, which corresponds to an about 45% increase. Incidentally, there was no particular difference between JMT-020 and JMT-020_long region.

Figure 15:
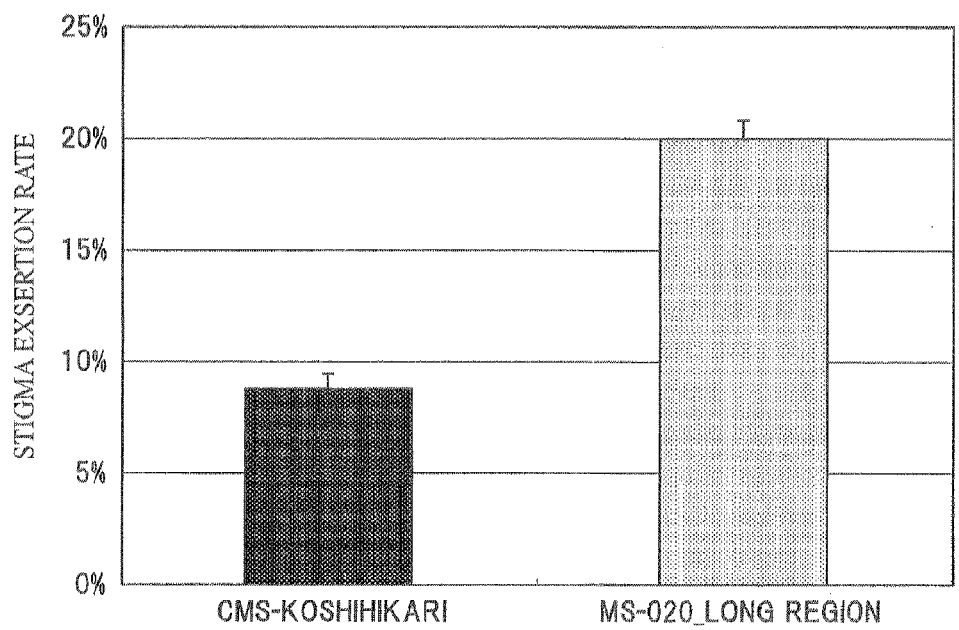
FIG. 15 is a view showing the results of a stigma exsertion rate measured for JMS-020_long region and CMS-Koshihikari in Example 1.
Figure 16:
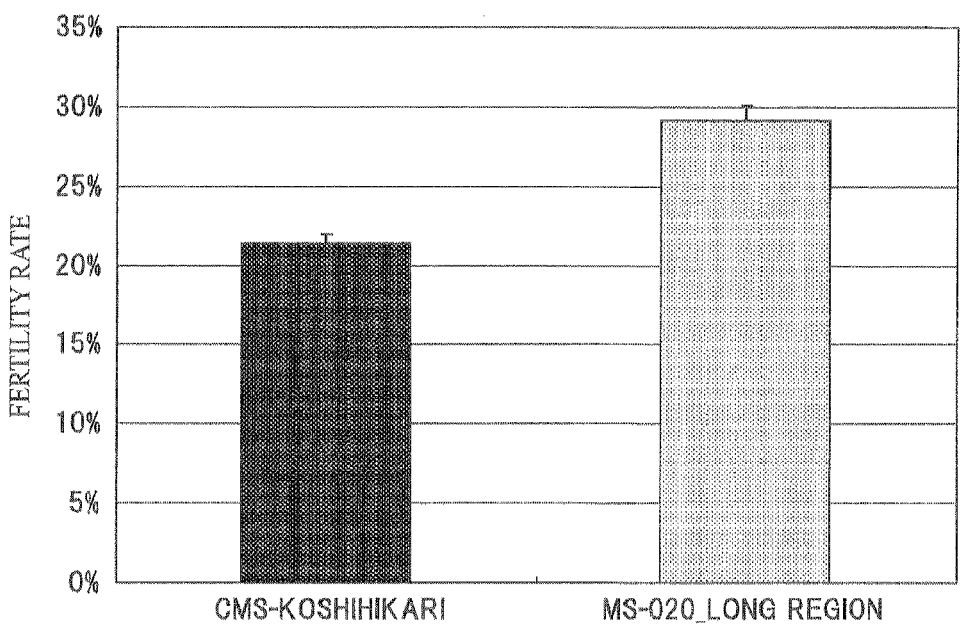
FIG. 16 is a view showing the results of a fertility rate measured on harvest of JMS-020_long region and CMS-Koshihikari in Example 1.

Next, in order to confirm seed production efficiency, first, JMS-020_long region and CMS-Koshihikari used as a seed parent were arranged between JMT-020_long region used as a pollen parent and distributed in a seed production field, followed by natural pollination. After confirming the fact that there was no change in terms of the heading time in rice lines of JMS-020_long region, CMS-Koshihikari and JMT-020_long region in this agricultural field, ears of rice were sampled after 7 days of ear emergence and a stigma exsertion rate was measured. Then, cultivation was continued and a fertility rate at the time of harvesting was measured. The measurement results of a stigma exsertion rate are shown in FIG. 15, and the measurement results of a fertility rate are shown in FIG. 16. As a result, JMS-020_long region exhibited significantly high stigma exsertion rate and fertility rate, as compared to CMS-Koshihikari. In particular, JMS-020_long region exhibited a stigma exsertion rate approximately 128% higher than CMS-Koshihikari. An improvement of a fertility rate of JMS-020_long region (that is, seed production efficiency) is believed to be due to an increased opportunity of the seed parent to receive pollen because a stigma exsertion rate is more improved in JMS-020_long region than in CMS-Koshihikari.

From these results, it is clear that when a rice cytoplasmic male sterile line of *Oryza sativa* L. cultivar Koshihikari into which the Cr1 gene derived from *Oryza nivara* has been introduced is used as a seed parent, seed production efficiency can be more improved, as compared to when a rice cytoplasmic male sterile line of *Oryza sativa* L. cultivar Koshihikari is used as a seed parent.

<Evaluation of Characteristic and Taste Quality of F1 Hybrid Line>

The F1 hybrid line (rice F1 hybrid line Hybrid Togo 1go) obtained by using JMS-021 as a seed parent, the F1 hybrid line (rice F1 hybrid line Hybrid Togo 2go) obtained by using JMS-022 as a seed parent, the F1 hybrid line (rice F1 hybrid line Hybrid Togo 3go) obtained by using JMS-023 as a seed parent, and the F1 hybrid line (rice F1 hybrid line Hybrid Togo 4go) obtained by using JMS-024 as a seed parent (for all of them, a pollen parent was restorer line JFR-004) were respectively cultivated. Similarly, the F1 hybrid line (rice F1 hybrid line Koshihikari/JFR-004) obtained by using CMS-Koshihikari as a seed parent was cultivated as a control. Characteristics of each F1 hybrid line were compared with those of *Oryza sativa* L. cultivar Koshihikari and *Oryza sativa* L. cultivar Nipponbare. Characteristics of each F1 hybrid line are given in Tables 6 and 7.

As a result, the rice F1 hybrid line Koshihikari/JFR-004 exhibited a significantly longer culm length, as compared to *Oryza sativa* L. cultivar Koshihikari. On the other hand, all of the rice F1 hybrid line Hybrid Togos 1 to 4go, which were obtained from the seed parent having a region containing the Habataki-derived sd1 gene, as shown in the seed parent, exhibited a culm length equal to or shorter than that of *Oryza sativa* L. cultivar Koshihikari.

Further, the rice F1 hybrid line Hybrid Togo 1go, the rice F1 hybrid line Hybrid Togo 3go, and the rice F1 hybrid line Koshihikari/JFR-004 became significantly later in terms of a heading time and a maturing term than *Oryza sativa* L. cultivar Koshihikari. On the other hand, a heading time and a maturing term of the rice F1 hybrid line Hybrid Togo 2go and the rice F1 hybrid line Hybrid Togo 4go, which were obtained from the seed parent having a region containing the Habataki-derived hd1 gene, were virtually the same as those of *Oryza sativa* L. cultivar Koshihikari, and became being converted into earlier growth than the rice F1 hybrid line Koshihikari/JFR-004 or the like.

Further, in the rice F1 hybrid line Hybrid Togo 3go and the rice F1 hybrid line Hybrid Togo 4go, which were obtained from a seed parent having semi-waxiness, grains having semi-waxiness were segregated as a ¼ fraction of total grains (a ¼ fraction of total grains was semi-waxy).

Incidentally, with regard to other characteristics, it could be seen that the rice F1 hybrid line Hybrid Togos 1 to 4go exhibit virtually the same characteristics as the rice F1 hybrid line Koshihikari/JFR-004.

From these results, it was confirmed that each F1 hybrid had inherited beneficial characteristics that the seed parent possessed.

TABLE 6

| Stage | Characteristic | Koshihikari | Nipponbare | Koshihikari/ JFR-004 | Hybrid Togo 1go | Hybrid Togo 2go | Hybrid Togo 3go | Hybrid Togo 4go |
|---|---|---|---|---|---|---|---|---|
| 40 | Leaf: Anthocyanine coloring | 1 (Absent) | 1 (Absent) | 1 (Absent) | 1 (Absent) | 1 (Absent) | 1 (Absent) | 1 (Absent) |
| | Leaf: Anthocyanine color of auricle | 1 (Absent) | 1 (Absent) | 1 (Absent) | 1 (Absent) | 1 (Absent) | 1 (Absent) | 1 (Absent) |
| 60 | Flag leaf: Posture of leaf blade (Initial observation) | 3 (Hemi-stand) | 3 (Hemi-stand) | 2 (Stand-Hemi-stand) | 2 (Stand-Hemi-stand) | 2 (Stand-Hemi-stand) | 2 (Stand-Hemi-stand) | 2 (Stand-Hemi-stand) |
| 90 | Flag leaf: Posture of leaf blade (Late observation) | 4 (Hemi-Horizontal stand) | 4 (Hemi-Horizontal stand) | 3 (Hemi-stand) | 3 (Hemi-stand) | 3 (Hemi-stand) | 3 (Hemi-stand) | 3 (Hemi-stand) |

TABLE 6-continued

| Stage | Characteristic | Koshihikari | Nipponbare | Koshihikari/ JFR-004 | Hybrid Togo 1go | Hybrid Togo 2go | Hybrid Togo 3go | Hybrid Togo 4go |
|---|---|---|---|---|---|---|---|---|
| 55 | Heading time (50% ear emergence) | 3 (July 26) | 5 (August 13) | 4 (August 7) | 4 (August 7) | 3 (July 25) | 4 (August 9) | 3 (July 23) |
| 65 | Lemma: Anthocyanine coloring of top part (Initial observation) | 1 (Absent) | 1 (Absent) | 1 (Absent) | 1 (Absent) | 1 (Absent) | 1 (Absent) | 1 (Absent) |
| 70 | Culm: Length (except for ear, except for floating rice) | 7 (95.2 cm) | 5 (83.0 cm) | 8 (120.2 cm) | 7 (103.8 cm) | 6 (87.2 cm) | 7 (99.8 cm) | 6 (89.4 cm) |
|  | Culm: Anthocyanine coloring of knot | 1 (Absent) | 1 (Absent) | 1 (Absent) | 1 (Absent) | 1 (Absent) | 1 (Absent) | 1 (Absent) |
| 72-90 | Ear: Length of main axis | 4 (21.2 cm) | 4 (22.8 cm) | 6 (30.7 cm) | 6 (28.8 cm) | 6 (27.1 cm) | 6 (29.7 cm) | 6 (27.4 cm) |
| 70 | Ear: ear number | 5 (12.0 ears/ spike) | 6 (16.0 ears/ spike) | 5 (11.8 ears/ spike) | 5 (10.8 ears/ spike) | 5 (11.0 ears/ spike) | 5 (13.2 ears/ spike) | 5 (12.0 ears/ spike) |
| 70-80 | Ear: distribution of arista | 1 (Only tip) | 1 (Only tip) | 1 (Only tip) | 1 (Only tip) | 1 (Only tip) | 1 (Only tip) | 1 (Only tip) |
| 60-80 | Small ear: Much or less of trichome of lemma | 1 (Absent or extremely small) | 1 (Absent or extremely small) | 1 (Absent or extremely small) | 1 (Absent or extremely small) | 1 (Absent or extremely small) | 1 (Absent or extremely small) | 1 (Absent or extremely small) |
| 80-90 | Small ear: Color of lemma tip (apiculus color) | 1 (White) | 1 (White) | 1 (White) | 1 (White) | 1 (White) | 1 (White) | 1 (White) |

TABLE 7

| Stage | Characteristic | Koshihikari | Nipponbare | Koshihikari/ JFR-004 | Hybrid Togo 1go | Hybrid Togo 2go | Hybrid Togo 3 go | Hybrid Togo 4go |
|---|---|---|---|---|---|---|---|---|
| 90 | Ear: Curvature extent of main axis | 5 (Hanging) | 5 (Hanging) | 5 (Hanging) | 5 (Hanging) | 5 (Hanging) | 5 (Hanging) | 5 (Hanging) |
|  | Ear: Ear type | 2 (Spindle-like) | 2 (Spindle-like) | 2 (Spindle-like) | 2 (Spindle-like) | 2 (Spindle-like) | 2 (Spindle-like) | 2 (Spindle-like) |
| 90 | Maturing stage | 3 (September 7) | 5 (September 25) | 6 (October 2) | 6 (October 2) | 4 (September 17) | 6 (October 2) | 4 (September 17) |
|  | Glume color | 1 (Yellowish white) | 1 (Yellowish white) | 1 (Yellowish white) | 1 (Yellowish white) | 1 (Yellowish white) | 1 (Yellowish white) | 1 (Yellowish white) |
|  | Glume color: Pattern | 1 (Absent) | 1 (Absent) | 1 (Absent) | 1 (Absent) | 1 (Absent) | 1 (Absent) | 1 (Absent) |
| 92 | Lemma: Anthocyanine coloring of top part (Late observation) | 1 (Absent) | 1 (Absent) | 1 (Absent) | 1 (Absent) | 1 (Absent) | 1 (Absent) | 1 (Absent) |
|  | Lemma: Length | 5 (2.2 mm) | 5 (2.2 mm) | 5 (2.3 mm) | 5 (2.3 mm) | 5 (2.3 mm) | 5 (2.3 mm) | 5 (2.3 mm) |
|  | Lemma: Color | 1 (Yellowish white) | 1 (Yellowish white) | 1 (Yellowish white) | 1 (Yellowish white) | 1 (Yellowish white) | 1 (Yellowish white) | 1 (Yellowish white) |
|  | Paddy: 1000 particles weight (mature) | 5 (23.9 g) | 5 (23.7 g) | 6 (25.1 g) | 6 (24.9 g) | 6 (26.3 g) | 6 (24.4 g) | 6 (26.3 g) |
|  | Paddy: Phenol reaction of palea | 1 (Absent) | 1 (Absent) | 1 (Absent) | 1 (Absent) | 1 (Absent) | 1 (Absent) | 1 (Absent) |

TABLE 7-continued

| Stage | Characteristic | Koshihikari | Nipponbare | Koshihikari/ JFR-004 | Hybrid Togo 1go | Hybrid Togo 2go | Hybrid Togo 3 go | Hybrid Togo 4go |
|---|---|---|---|---|---|---|---|---|
| | Brown rice: Length | 5 (Intermediate, 5.17 mm) | 5 (Intermediate, 5.26 mm) | 5 (Intermediate, 5.52 mm) | 5 (Intermediate, 5.42 mm) | 5 (Intermediate, 5.59 mm) | 5 (Intermediate, 5.51 mm) | 5 (Intermediate, 5.59 mm) |
| | Brown rice: Width | 5 (Intermediate, 2.98 mm) | 5 (Intermediate, 2.95 mm) | 5 (Intermediate, 2.94 mm) | 5 (Intermediate, 2.84 mm) | 5 (Intermediate, 2.99 mm) | 5 (Intermediate, 2.89 mm) | 5 (Intermediate, 2.97 mm) |
| | Brown rice: Shape (as viewed from side) | 2 (Half circular) | 2 (Half circular) | 2 (Half circular) | 2 (Half circular) | 2 (Half circular) | 2 (Half circular) | 2 (Half circular) |
| | Brown rice: Color | 2 (Brown) | 2 (Brown) | 2 (Brown) | 2 (Brown) | 2 (Brown) | 2 (Brown) | 2 (Brown) |
| | Brown rice: Fragrances | 1 (Absent) | 1 (Absent) | 1 (Absent) | 1 (Absent) | 1 (Absent) | 1 (Absent) | 1 (Absent) |
| | Endosperm: Type | 3 (non-waxy) | 3 (non-waxy) | 3 (non-waxy) | 3 (non-waxy) | 3 (non-waxy) | 2 (semi-waxy) | 2 (semi-waxy) |

Further, the taste quality of rice harvested from these F1 hybrids was evaluated using a rice taste measuring system (Toyo Rice Polishing Machine Factory, Japan). The measurement results are given in Table 8. As a result, Koshihikari exhibited a score of 64.5, whereas F1 lines exhibited a score of 63.0 to 68.0, and therefore it can be seen that all of the F1 hybrid lines are an excellent good taste-quality line like *Oryza sativa* L. cultivar Koshihikari.

TABLE 8

| Name of rice line | Taste value |
|---|---|
| Koshihikari | 64.5 |
| Hybrid Togo 1go | 64.5 |
| Hybrid Togo 2go | 63.0 |
| Hybrid Togo 3go | 68.0 |
| Hybrid Togo 4go | 63.5 |

INDUSTRIAL APPLICABILITY

The method for producing a rice F1 seed in accordance with the present invention is capable of producing a seed of a rice F1 hybrid with higher efficiency of selection, as compared to when a cytoplasmic male sterile line of *Oryza sativa* L. cultivar Koshihikari is used as a seed parent, and therefore the method can be utilized, particularly, in the field of plant breeding.

The present invention drawn to rice line Hybrid Togo 1go, Hybrid Togo 2go, Hybrid Togo 3go, and Hybrid Togo 4go, and JMS-019, JSM-020, JMS-021, JMS-022, JMS-023, and JMS-024. Such rice line will be, irrevocably and without restriction or condition, released to the public upon the issuance of a patent from the instant application.

SEQUENCE LIST

[FIG. 1]
MODAN-DERIVED CHROMOSOME FRAGMENT
KOSHIHIKARI CHROMOSOME
[FIG. 2]
O. NIVARA-DERIVED CHROMOSOME FRAGMENT
KOSHIHIKARI CHROMOSOME
[FIG. 3]
HABATAKI-DERIVED CHROMOSOME FRAGMENT
KOSHIHIKARI CHROMOSOME
[FIG. 4]
HABATAKI-DERIVED CHROMOSOME FRAGMENT
KOSHIHIKARI CHROMOSOME
[FIG. 5]
HABATAKI-DERIVED CHROMOSOME FRAGMENT
KOSHIHIKARI CHROMOSOME
[FIG. 6]
MODAN-DERIVED CHROMOSOME FRAGMENT
KOSHIHIKARI CHROMOSOME
[FIG. 7]
O. NIVARA-DERIVED CHROMOSOME FRAGMENT
KOSHIHIKARI CHROMOSOME
[FIG. 8]
O. NIVARA-DERIVED CHROMOSOME FRAGMENT
KOSHIHIKARI CHROMOSOME
[FIG. 9]
FOREIGN LINE-DERIVED CHROMOSOME FRAGMENT
KOSHIHIKARI CHROMOSOME
[FIG. 10]
FOREIGN LINE-DERIVED CHROMOSOME FRAGMENT
KOSHIHIKARI CHROMOSOME
[FIG. 11]
FOREIGN LINE-DERIVED CHROMOSOME FRAGMENT
KOSHIHIKARI CHROMOSOME
[FIG. 12]
FOREIGN LINE-DERIVED CHROMOSOME FRAGMENT
KOSHIHIKARI CHROMOSOME
[FIG. 13]
KOSHIHIKARI
PATHOGENIC DEGREE
AFTER 11 DAYS
AFTER 14 DAYS
[FIG. 14]
STIGMA EXSERTION RATE
KOSHIHIKARI
LONG REGION
[FIG. 15]
STIGMA EXSERTION RATE
KOSHIHIKARI
LONG REGION
[FIG. 16]
FERTILITY RATE
KOSHIHIKARI
LONG REGION

What is claimed is:

1. A method for producing a rice F1 seed, comprising:
crossing a rice male sterile line containing a Pb1 gene derived from a rice (*Oryza sativa* L) cultivar Modan and a Cr1 gene derived from *Oryza nivara*, as a seed parent, with a rice fertility restorer line as a pollen parent;
collecting a first filial generation seed (F1 seed) from the post-crossing seed parent, the rice male sterile line further comprises one or more genes selected from the group consisting of an sd1 gene derived from *Oryza sativa* L. cultivar Habataki, a Gn1 gene derived from *Oryza sativa* L. cultivar Habataki, and an hd1 gene derived from *Oryza sativa* L. cultivar Habataki.

2. The method for producing a rice F1 seed according to claim 1, wherein the rice male sterile line further exhibits semi-waxiness.

3. The method for producing a rice F1 seed according to claim 1, wherein the rice male sterile line is a cytoplasmic male sterile line selected from the group consisting of a rice cytoplasmic male sterile line JMS-021, a rice cytoplasmic male sterile line JMS-022, a rice cytoplasmic male sterile line JMS-023, and a rice cytoplasmic male sterile line JMS-024.

4. A rice F1 hybrid line Hybrid Togo 1 go, a representative sample of seed of said line has been deposited under accession FERM BP-11457.

5. A rice F1 hybrid line Hybrid Togo 2go, a representative sample of seed of said line has been deposited under accession FERM BP-11458.

6. A rice F1 hybrid line Hybrid Togo 3go, a representative sample of seed of said line has been deposited under accession FERM BP-11459.

7. A rice F1 hybrid line Hybrid Togo 4go, a representative sample of seed of said line deposited under accession FERM BP-11460.

8. A rice male sterile line comprising a Pb1 gene derived from rice (*Oryza sativa* L) cultivar Modan, a Cr1 gene derived from *Oryza nivara*, and
the rice male sterile line further comprising one or more genes selected from the group consisting of an sd1 gene derived from *Oryza sativa* L. cultivar Habataki, a Gn1 gene derived from *Oryza sativa* L. cultivar Habataki, and an hd1 gene derived from *Oryza sativa* L. cultivar Habataki.

9. The rice male sterile line according to claim 8, further exhibiting semi-waxiness.

10. A rice cytoplasmic male sterile line JMS-021, a representative sample of seed of said line has been deposited under accession FERM BP-11461.

11. A rice cytoplasmic male sterile line JMS-022, a representative sample of seed of said line has been deposited under accession FERM BP-11462.

12. A rice cytoplasmic male sterile line JMS-023, a representative sample of seed of said line has been deposited under accession FERM BP-11463.

13. A rice cytoplasmic male sterile line JMS-024, a representative sample of seed of said line has been deposited under accession FERM BP-11464.

* * * * *

SEQUENCE LISTING

```
<160> NUMBER OF SEQ ID NOS: 97

<210> SEQ ID NO 1
<211> LENGTH: 24
<212> TYPE: DNA
<213> ORGANISM: Oryza sativa
<220> FEATURE:
<223> OTHER INFORMATION: DNA marker: Upper Sequence of SP-2650

<400> SEQUENCE: 1 gctaataacct tcctatgaaa gctc                                              24

<210> SEQ ID NO 2
<211> LENGTH: 18
<212> TYPE: DNA
<213> ORGANISM: Oryza sativa
<220> FEATURE:
<223> OTHER INFORMATION: DNA marker: Lower Sequence of SP-2650

<400> SEQUENCE: 2
cgctctgcaa aaggcaag                                                     18

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      rice SNP primer of SP-2650

<400> SEQUENCE: 3
gtgtgtaatt ggagacaaag ca                                                22

<210> SEQ ID NO 4
<211> LENGTH: 20
<212> TYPE: DNA
<213> ORGANISM: Oryza sativa
<220> FEATURE:
<223> OTHER INFORMATION: DNA marker: Upper Sequence of SP-4234

<400> SEQUENCE: 4
agctatctcc agatctgagc                                                   20

<210> SEQ ID NO 5
<211> LENGTH: 20
<212> TYPE: DNA
<213> ORGANISM: Oryza sativa
<220> FEATURE:
<223> OTHER INFORMATION: DNA marker: Lower Sequence of SP-4234

<400> SEQUENCE: 5
ccgatactac gatacgatcc                                                   20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      rice SNP primer of SP-4234

<400> SEQUENCE: 6
cttgcttatg acgtggcatg                                                   20
```

```
<210> SEQ ID NO 7
<211> LENGTH: 22
<212> TYPE: DNA
<213> ORGANISM: Oryza sativa
<220> FEATURE:
<223> OTHER INFORMATION: DNA marker: Upper Sequence of SP-5290

<400> SEQUENCE: 7
ctaaccttgc aaatgttgtg cc                                              22

<210> SEQ ID NO 8
<211> LENGTH: 22
<212> TYPE: DNA
<213> ORGANISM: Oryza sativa
<220> FEATURE:
<223> OTHER INFORMATION: DNA marker: Lower Sequence of SP-5290

<400> SEQUENCE: 8
cagtaagttc agtgatgttg cc                                              22

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      rice SNP primer of SP-5290

<400> SEQUENCE: 9
ccttaacctg gggcagctca gt                                              22

<210> SEQ ID NO 10
<211> LENGTH: 20
<212> TYPE: DNA
<213> ORGANISM: Oryza sativa
<220> FEATURE:
<223> OTHER INFORMATION: DNA marker: Upper Sequence of SP-5384

<400> SEQUENCE: 10
ttcgcttttt cctccagctc                                                 20

<210> SEQ ID NO 11
<211> LENGTH: 20
<212> TYPE: DNA
<213> ORGANISM: Oryza sativa
<220> FEATURE:
<223> OTHER INFORMATION: DNA marker: Lower Sequence of SP-5384

<400> SEQUENCE: 11
tagcatgaag aggagtaggg                                                 20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      rice SNP primer of SP-5384

<400> SEQUENCE: 12
tactcctaaa tcgccacatg                                                 20

<210> SEQ ID NO 13
<211> LENGTH: 20
<212> TYPE: DNA
<213> ORGANISM: Oryza sativa
```

```
<220> FEATURE:
<223> OTHER INFORMATION: DNA marker: Upper Sequence of SP-5569

<400> SEQUENCE: 13
gttggtgcaa tacatagacc                                                 20

<210> SEQ ID NO 14
<211> LENGTH: 20
<212> TYPE: DNA
<213> ORGANISM: Oryza sativa
<220> FEATURE:
<223> OTHER INFORMATION: DNA marker: Lower Sequence of SP-5569

<400> SEQUENCE: 14
tactgatctg gctcatgcag                                                 20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      rice SNP primer of SP-5569

<400> SEQUENCE: 15
acaatggcca gattgtgtcc                                                 20

<210> SEQ ID NO 16
<211> LENGTH: 20
<212> TYPE: DNA
<213> ORGANISM: Oryza sativa
<220> FEATURE:
<223> OTHER INFORMATION: DNA marker: Upper Sequence of SP-4236

<400> SEQUENCE: 16
aagcacaagg cttctcgagg                                                 20

<210> SEQ ID NO 17
<211> LENGTH: 22
<212> TYPE: DNA
<213> ORGANISM: Oryza sativa
<220> FEATURE:
<223> OTHER INFORMATION: DNA marker: Lower Sequence of SP-4236

<400> SEQUENCE: 17
gcaggaattt gattctcctg gg                                              22

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      rice SNP primer of SP-4236

<400> SEQUENCE: 18
ctttctacga ctgttgatac ggt                                             23

<210> SEQ ID NO 19
<211> LENGTH: 18
<212> TYPE: DNA
<213> ORGANISM: Oryza sativa
<220> FEATURE:
<223> OTHER INFORMATION: DNA marker: Upper Sequence of SP-2966
```

-continued

<400> SEQUENCE: 19
actagaggag cactgcag                                                    18

<210> SEQ ID NO 20
<211> LENGTH: 18
<212> TYPE: DNA
<213> ORGANISM: Oryza sativa
<220> FEATURE:
<223> OTHER INFORMATION: DNA marker: Lower Sequence of SP-2966

<400> SEQUENCE: 20
catgcctgca ttcctgct                                                    18

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence: Synthetic
      rice SNP primer of SP-2966

<400> SEQUENCE: 21
acaggcaaac gttgcctcg                                                   19

<210> SEQ ID NO 22
<211> LENGTH: 19
<212> TYPE: DNA
<213> ORGANISM: Oryza sativa
<220> FEATURE:
<223> OTHER INFORMATION: DNA marker: Upper Sequence of SP-3819

<400> SEQUENCE: 22
ggtttgtgct ggtcatggc                                                   19

<210> SEQ ID NO 23
<211> LENGTH: 20
<212> TYPE: DNA
<213> ORGANISM: Oryza sativa
<220> FEATURE:
<223> OTHER INFORMATION: DNA marker: Lower Sequence of SP-3819

<400> SEQUENCE: 23
actaaccata acgcgagcct                                                  20

<210> SEQ ID NO 24
<211> LENGTH: 17
<212> TYPE: DNA
<213> ORGANISM: Artificial Sequence
<220> FEATURE:
<223> OTHER INFORMATION: Description of Artificial Sequence: Synthetic
      rice SNP primer of SP-3819

<400> SEQUENCE: 24
tcccagatcg aatcgag                                                     17

<210> SEQ ID NO 25
<211> LENGTH: 19
<212> TYPE: DNA
<213> ORGANISM: Oryza sativa
<220> FEATURE:
<223> OTHER INFORMATION: DNA marker: Upper Sequence of SP-4141

<400> SEQUENCE: 25
ctagcgtggg caatgacta                                                   19

```
<210> SEQ ID NO 26
<211> LENGTH: 18
<212> TYPE: DNA
<213> ORGANISM: Oryza sativa
<220> FEATURE:
<223> OTHER INFORMATION: DNA marker: Lower Sequence of SP-4141

<400> SEQUENCE: 26
ctaaaccgag gtggctag                                                 18

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      rice SNP primer of SP-4141

<400> SEQUENCE: 27
atctggtagc tgatcaaccc                                               20

<210> SEQ ID NO 28
<211> LENGTH: 20
<212> TYPE: DNA
<213> ORGANISM: Oryza sativa
<220> FEATURE:
<223> OTHER INFORMATION: DNA marker: Upper Sequence of SP-3823

<400> SEQUENCE: 28
tgctgcataa gcgtacatgg                                               20

<210> SEQ ID NO 29
<211> LENGTH: 20
<212> TYPE: DNA
<213> ORGANISM: Oryza sativa
<220> FEATURE:
<223> OTHER INFORMATION: DNA marker: Lower Sequence of SP-3823

<400> SEQUENCE: 29
gaaccaatgg aatgctggct                                               20

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic
      rice SNP primer of SP-3823

<400> SEQUENCE: 30
ggatatgatc catatggtta tg                                            22

<210> SEQ ID NO 31
<211> LENGTH: 20
<212> TYPE: DNA
<213> ORGANISM: Oryza sativa
<220> FEATURE:
<223> OTHER INFORMATION: DNA marker: Upper Sequence of SP-3826

<400> SEQUENCE: 31
catcttgcgg ttgtagttgg                                               20

<210> SEQ ID NO 32
<211> LENGTH: 22
<212> TYPE: DNA
<213> ORGANISM: Oryza sativa
```

<220> FEATURE:
<223> OTHER INFORMATION: DNA marker: Lower Sequence of SP-3826

<400> SEQUENCE: 32
caaggaggaa aatatgccag ca        22

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      rice SNP primer of SP-3826

<400> SEQUENCE: 33
atcgagaata tcacaatgcg        20

<210> SEQ ID NO 34
<211> LENGTH: 22
<212> TYPE: DNA
<213> ORGANISM: Oryza sativa
<220> FEATURE:
<223> OTHER INFORMATION: DNA marker: Upper Sequence of SP-306

<400> SEQUENCE: 34
catattctac agcgttctcg tc        22

<210> SEQ ID NO 35
<211> LENGTH: 19
<212> TYPE: DNA
<213> ORGANISM: Oryza sativa
<220> FEATURE:
<223> OTHER INFORMATION: DNA marker: Lower Sequence of SP-306

<400> SEQUENCE: 35
aacaccaagg gcgatcgag        19

<210> SEQ ID NO 36
<211> LENGTH: 17
<212> TYPE: DNA
<213> ORGANISM: Artificial Sequence
<220> FEATURE:
<223> OTHER INFORMATION: Description of Artificial Sequence: Synthetic
      rice SNP primer of SP-306

<400> SEQUENCE: 36
ataccgagcc cagcaat        17

<210> SEQ ID NO 37
<211> LENGTH: 20
<212> TYPE: DNA
<213> ORGANISM: Oryza sativa
<220> FEATURE:
<223> OTHER INFORMATION: DNA marker: Upper Sequence of SP-2058

<400> SEQUENCE: 37
tgctacaact gtacacactg        20

<210> SEQ ID NO 38
<211> LENGTH: 20
<212> TYPE: DNA
<213> ORGANISM: Oryza sativa
<220> FEATURE:
<223> OTHER INFORMATION: DNA marker: Lower Sequence of SP-2058

```
<400> SEQUENCE: 38
gctcgaagac acattggttc                                              20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      rice SNP primer of SP-2058

<400> SEQUENCE: 39
agtagaaaaa ccaacacctt                                              20

<210> SEQ ID NO 40
<211> LENGTH: 19
<212> TYPE: DNA
<213> ORGANISM: Oryza sativa
<220> FEATURE:
<223> OTHER INFORMATION: DNA marker: Upper Sequence of SP-4009

<400> SEQUENCE: 40
ccgttatgtg cctgtatgg                                               19

<210> SEQ ID NO 41
<211> LENGTH: 20
<212> TYPE: DNA
<213> ORGANISM: Oryza sativa
<220> FEATURE:
<223> OTHER INFORMATION: DNA marker: Lower Sequence of SP-4009

<400> SEQUENCE: 41
tgttgcagga aggtgacagg                                              20

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      rice SNP primer of SP-4009

<400> SEQUENCE: 42
ttggaaggaa catctagcac a                                            21

<210> SEQ ID NO 43
<211> LENGTH: 18
<212> TYPE: DNA
<213> ORGANISM: Oryza sativa
<220> FEATURE:
<223> OTHER INFORMATION: DNA marker: Upper Sequence of G2003

<400> SEQUENCE: 43
cacagcgctc acttctca                                                18

<210> SEQ ID NO 44
<211> LENGTH: 20
<212> TYPE: DNA
<213> ORGANISM: Oryza sativa
<220> FEATURE:
<223> OTHER INFORMATION: DNA marker: Lower Sequence of G2003

<400> SEQUENCE: 44
tgcaatgtcg tccaccatcg                                              20
```

```
<210> SEQ ID NO 45
<211> LENGTH: 18
<212> TYPE: DNA
<213> ORGANISM: Oryza sativa
<220> FEATURE:
<223> OTHER INFORMATION: DNA marker: Upper Sequence of G2002

<400> SEQUENCE: 45
cacagcgctc acttctca                                                 18

<210> SEQ ID NO 46
<211> LENGTH: 19
<212> TYPE: DNA
<213> ORGANISM: Oryza sativa
<220> FEATURE:
<223> OTHER INFORMATION: DNA marker: Lower Sequence of G2002

<400> SEQUENCE: 46
atgatcgtca gcgacagct                                                19

<210> SEQ ID NO 47
<211> LENGTH: 18
<212> TYPE: DNA
<213> ORGANISM: Oryza sativa
<220> FEATURE:
<223> OTHER INFORMATION: DNA marker: Upper Sequence of SP-462

<400> SEQUENCE: 47
aactccagcg tgctaagc                                                 18

<210> SEQ ID NO 48
<211> LENGTH: 18
<212> TYPE: DNA
<213> ORGANISM: Oryza sativa
<220> FEATURE:
<223> OTHER INFORMATION: DNA marker: Lower Sequence of SP-462

<400> SEQUENCE: 48
gcattgcatg caggatcg                                                 18

<210> SEQ ID NO 49
<211> LENGTH: 19
<212> TYPE: DNA
<213> ORGANISM: Artificial Sequence
<220> FEATURE:
<223> OTHER INFORMATION: Description of Artificial Sequence: Synthetic
      rice SNP primer of SP-462

<400> SEQUENCE: 49
agagcccttc actttcagc                                                19

<210> SEQ ID NO 50
<211> LENGTH: 18
<212> TYPE: DNA
<213> ORGANISM: Oryza sativa
<220> FEATURE:
<223> OTHER INFORMATION: DNA marker: Upper Sequence of SP-1259

<400> SEQUENCE: 50
aaggctgatg agcactgc                                                 18

<210> SEQ ID NO 51
<211> LENGTH: 19
<212> TYPE: DNA
<213> ORGANISM: Oryza sativa
<220> FEATURE:
<223> OTHER INFORMATION: DNA marker: Lower Sequence of SP-1259
```

-continued

<400> SEQUENCE: 51
ggcattgtgg aagctcttc                                           19

<210> SEQ ID NO 52
<211> LENGTH: 17
<212> TYPE: DNA
<213> ORGANISM: Artificial Sequence
<220> FEATURE:
<223> OTHER INFORMATION: Description of Artificial Sequence: Synthetic
      rice SNP primer of SP-1259

<400> SEQUENCE: 52
tctcctttcg gagtccc                                             17

<210> SEQ ID NO 53
<211> LENGTH: 22
<212> TYPE: DNA
<213> ORGANISM: Oryza sativa
<220> FEATURE:
<223> OTHER INFORMATION: DNA marker: Upper Sequence of SP-477

<400> SEQUENCE: 53
gctatgttga acaagttcgc tg                                       22

<210> SEQ ID NO 54
<211> LENGTH: 20
<212> TYPE: DNA
<213> ORGANISM: Oryza sativa
<220> FEATURE:
<223> OTHER INFORMATION: DNA marker: Lower Sequence of SP-477

<400> SEQUENCE: 54
catcgtggac agcaatcttg                                          20

<210> SEQ ID NO 55
<211> LENGTH: 19
<212> TYPE: DNA
<213> ORGANISM: Artificial Sequence
<220> FEATURE:
<223> OTHER INFORMATION: Description of Artificial Sequence: Synthetic
      rice SNP primer of SP-477

<400> SEQUENCE: 55
gtatagttag tcatgtgcc                                           19

<210> SEQ ID NO 56
<211> LENGTH: 20
<212> TYPE: DNA
<213> ORGANISM: Oryza sativa
<220> FEATURE:
<223> OTHER INFORMATION: DNA marker: Upper Sequence of SP-156

<400> SEQUENCE: 56
ggaattcaga gacaacatgg                                          20

<210> SEQ ID NO 57
<211> LENGTH: 22
<212> TYPE: DNA
<213> ORGANISM: Oryza sativa
<220> FEATURE:
<223> OTHER INFORMATION: DNA marker: Lower Sequence of SP-156

<400> SEQUENCE: 57
gcttcagtgt tgtgtgattc tg                                       22

-continued

```
<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      rice SNP primer of SP-156

<400> SEQUENCE: 58
aacgagttct acaatgctgc                                                  20

<210> SEQ ID NO 59
<211> LENGTH: 21
<212> TYPE: DNA
<213> ORGANISM: Oryza sativa
<220> FEATURE:
<223> OTHER INFORMATION: DNA marker: Upper Sequence of SP-2032

<400> SEQUENCE: 59
cattgagtcc atttcctctg c                                                21

<210> SEQ ID NO 60
<211> LENGTH: 20
<212> TYPE: DNA
<213> ORGANISM: Oryza sativa
<220> FEATURE:
<223> OTHER INFORMATION: DNA marker: Lower Sequence of SP-2032

<400> SEQUENCE: 60
gcagctccaa gaatgactac                                                  20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      rice SNP primer of SP-2032

<400> SEQUENCE: 61
attggtgcta gagcaactac                                                  20

<210> SEQ ID NO 62
<211> LENGTH: 20
<212> TYPE: DNA
<213> ORGANISM: Oryza sativa
<220> FEATURE:
<223> OTHER INFORMATION: DNA marker: Upper Sequence of SP-170

<400> SEQUENCE: 62
gtgagacata gactatccac                                                  20

<210> SEQ ID NO 63
<211> LENGTH: 19
<212> TYPE: DNA
<213> ORGANISM: Oryza sativa
<220> FEATURE:
<223> OTHER INFORMATION: DNA marker: Lower Sequence of SP-170

<400> SEQUENCE: 63
acgcgtacgc cacatagac                                                   19

<210> SEQ ID NO 64
<211> LENGTH: 19
<212> TYPE: DNA
<213> ORGANISM: Artificial Sequence
```

```
<220> FEATURE:
<223> OTHER INFORMATION: Description of Artificial Sequence: Synthetic
      rice SNP primer of SP-170

<400> SEQUENCE: 64
agggtgagga atgtccggt                                                   19

<210> SEQ ID NO 65
<211> LENGTH: 20
<212> TYPE: DNA
<213> ORGANISM: Oryza sativa
<220> FEATURE:
<223> OTHER INFORMATION: DNA marker: Upper Sequence of SP-4028

<400> SEQUENCE: 65
gcagtacctg ccttactacg                                                  20

<210> SEQ ID NO 66
<211> LENGTH: 20
<212> TYPE: DNA
<213> ORGANISM: Oryza sativa
<220> FEATURE:
<223> OTHER INFORMATION: DNA marker: Lower Sequence of SP-4028

<400> SEQUENCE: 66
catttcatgc gagtggtgac                                                  20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      rice SNP primer of SP-4028

<400> SEQUENCE: 67
tgcacgaatc ttggccagag                                                  20

<210> SEQ ID NO 68
<211> LENGTH: 24
<212> TYPE: DNA
<213> ORGANISM: Oryza sativa
<220> FEATURE:
<223> OTHER INFORMATION: DNA marker: Upper Sequence of SP-4038

<400> SEQUENCE: 68
cttaaactca acttgcacaa gtag                                             24

<210> SEQ ID NO 69
<211> LENGTH: 20
<212> TYPE: DNA
<213> ORGANISM: Oryza sativa
<220> FEATURE:
<223> OTHER INFORMATION: DNA marker: Lower Sequence of SP-4038

<400> SEQUENCE: 69
actgccgaca tgttactgtc                                                  20

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic
      rice SNP primer of SP-4038
```

<400> SEQUENCE: 70
gtcccacctg aaacatatcc a                                              21

<210> SEQ ID NO 71
<211> LENGTH: 22
<212> TYPE: DNA
<213> ORGANISM: Oryza sativa
<220> FEATURE:
<223> OTHER INFORMATION: DNA marker: Upper Sequence of SP-4030

<400> SEQUENCE: 71
tctttgattc tttggtcgat cg                                             22

<210> SEQ ID NO 72
<211> LENGTH: 20
<212> TYPE: DNA
<213> ORGANISM: Oryza sativa
<220> FEATURE:
<223> OTHER INFORMATION: DNA marker: Lower Sequence of SP-4030

<400> SEQUENCE: 72
gcgtacgaga gctatagagc                                                20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      rice SNP primer of SP-4030

<400> SEQUENCE: 73
atggatccgt ggatcgatcg                                                20

<210> SEQ ID NO 74
<211> LENGTH: 20
<212> TYPE: DNA
<213> ORGANISM: Oryza sativa
<220> FEATURE:
<223> OTHER INFORMATION: DNA marker: Upper Sequence of SP-262

<400> SEQUENCE: 74
gcagcaggac aaaggctaac                                                20

<210> SEQ ID NO 75
<211> LENGTH: 20
<212> TYPE: DNA
<213> ORGANISM: Oryza sativa
<220> FEATURE:
<223> OTHER INFORMATION: DNA marker: Lower Sequence of SP-262

<400> SEQUENCE: 75
acccttcttc aagctccatc                                                20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      rice SNP primer of SP-262

<400> SEQUENCE: 76
tcacaaccgg accagatgac                                                20

-continued

```
<210> SEQ ID NO 77
<211> LENGTH: 21
<212> TYPE: DNA
<213> ORGANISM: Oryza sativa
<220> FEATURE:
<223> OTHER INFORMATION: DNA marker: Upper Sequence of SP-2229

<400> SEQUENCE: 77
caatctggga ttctggatca g                                          21

<210> SEQ ID NO 78
<211> LENGTH: 20
<212> TYPE: DNA
<213> ORGANISM: Oryza sativa
<220> FEATURE:
<223> OTHER INFORMATION: DNA marker: Lower Sequence of SP-2229

<400> SEQUENCE: 78
agctcagtat cacggacttg                                            20

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: Synthetic
      rice SNP primer of SP-2229

<400> SEQUENCE: 79
gtctctttta acacaccttL c                                          21

<210> SEQ ID NO 80
<211> LENGTH: 22
<212> TYPE: DNA
<213> ORGANISM: Oryza sativa
<220> FEATURE:
<223> OTHER INFORMATION: DNA marker: Upper Sequence of SP-2513

<400> SEQUENCE: 80
gcgaaaagat gaggatgtac ac                                         22

<210> SEQ ID NO 81
<211> LENGTH: 20
<212> TYPE: DNA
<213> ORGANISM: Oryza sativa
<220> FEATURE:
<223> OTHER INFORMATION: DNA marker: Lower Sequence of SP-2513

<400> SEQUENCE: 81
ccgtaggcct ttgtcaagtg                                            20

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
      rice SNP primer of SP-2513

<400> SEQUENCE: 82
ctttaatggt ggcttatgtc                                            20

<210> SEQ ID NO 83
<211> LENGTH: 22
<212> TYPE: DNA
<213> ORGANISM: Oryza sativa
```

```
<220> FEATURE:
<223> OTHER INFORMATION: DNA marker: Upper Sequence of SP-586

<400> SEQUENCE: 83
gctaggacaa gcttatttca gc                                              22

<210> SEQ ID NO 84
<211> LENGTH: 18
<212> TYPE: DNA
<213> ORGANISM: Oryza sativa
<220> FEATURE:
<223> OTHER INFORMATION: DNA marker: Lower Sequence of SP-586

<400> SEQUENCE: 84
tcacgccgat caagaacg                                                   18

<210> SEQ ID NO 85
<211> LENGTH: 24
<212> TYPE: DNA
<213> ORGANISM: Artificial Sequence
<220> FEATURE:
<223> OTHER INFORMATION: Description of Artificial Sequence: Synthetic
      rice SNP primer of SP-586

<400> SEQUENCE: 85
cataatttat cgccattttc gcat                                            24

<210> SEQ ID NO 86
<211> LENGTH: 18
<212> TYPE: DNA
<213> ORGANISM: Oryza sativa
<220> FEATURE:
<223> OTHER INFORMATION: DNA marker: Upper Sequence of SP-2254

<400> SEQUENCE: 86
aggcccttgt actggtac                                                   18

<210> SEQ ID NO 87
<211> LENGTH: 21
<212> TYPE: DNA
<213> ORGANISM: Oryza sativa
<220> FEATURE:
<223> OTHER INFORMATION: DNA marker: Lower Sequence of SP-2254

<400> SEQUENCE: 87
gtacacaata gttggtgcac c                                               21

<210> SEQ ID NO 88
<211> LENGTH: 19
<212> TYPE: DNA
<213> ORGANISM: Artificial Sequence
<220> FEATURE:
<223> OTHER INFORMATION: Description of Artificial Sequence: Synthetic
      rice SNP primer of SP-2254

<400> SEQUENCE: 88
catgataagg tactcctgg                                                  19

<210> SEQ ID NO 89
<211> LENGTH: 22
<212> TYPE: DNA
<213> ORGANISM: Oryza sativa
<220> FEATURE:
<223> OTHER INFORMATION: DNA marker: Upper Sequence of SP-1603
```

```
<400> SEQUENCE: 89
cctagtccct aaagatctca tg                                              22

<210> SEQ ID NO 90
<211> LENGTH: 21
<212> TYPE: DNA
<213> ORGANISM: Oryza sativa
<220> FEATURE:
<223> OTHER INFORMATION: DNA marker: Lower Sequence of SP-1603

<400> SEQUENCE: 90
gatagacatg acggagaagt g                                               21

<210> SEQ ID NO 91
<211> LENGTH: 19
<212> TYPE: DNA
<213> ORGANISM: Artificial Sequence
<220> FEATURE:
<223> OTHER INFORMATION: Description of Artificial Sequence: Synthetic
      rice SNP primer of SP-1603

<400> SEQUENCE: 91
gggtggtgtt atctctagt                                                  19

<210> SEQ ID NO 92
<211> LENGTH: 20
<212> TYPE: DNA
<213> ORGANISM: Oryza sativa
<220> FEATURE:
<223> OTHER INFORMATION: DNA marker: Upper Sequence of SP-604

<400> SEQUENCE: 92
gcgcaaattc cttcagtcac                                                 20

<210> SEQ ID NO 93
<211> LENGTH: 19
<212> TYPE: DNA
<213> ORGANISM: Oryza sativa
<220> FEATURE:
<223> OTHER INFORMATION: DNA marker: Lower Sequence of SP-604

<400> SEQUENCE: 93
cagtttcagg tggaagacc                                                  19

<210> SEQ ID NO 94
<211> LENGTH: 22
<212> TYPE: DNA
<213> ORGANISM: Artificial Sequence
<220> FEATURE:
<223> OTHER INFORMATION: Description of Artificial Sequence: Synthetic
      rice SNP primer of SP-604

<400> SEQUENCE: 94
caagtttctt cctctcattt tc                                              22

<210> SEQ ID NO 95
<211> LENGTH: 20
<212> TYPE: DNA
<213> ORGANISM: Oryza sativa
<220> FEATURE:
<223> OTHER INFORMATION: DNA marker: Upper Sequence of SP-1635

<400> SEQUENCE: 95
taggagtgaa tggcggtaag                                                 20
```

```
<210> SEQ ID NO 96
<211> LENGTH: 22
<212> TYPE: DNA
<213> ORGANISM: Oryza sativa
<220> FEATURE:
<223> OTHER INFORMATION: DNA marker: Lower Sequence of SP-1635

<400> SEQUENCE: 96
gtatatcccg acaatagtcc tg                                              22

<210> SEQ ID NO 97
<211> LENGTH: 24
<212> TYPE: DNA
<213> ORGANISM: Artificial Sequence
<220> FEATURE:
<223> OTHER INFORMATION: Description of Artificial Sequence: Synthetic
      rice SNP primer of SP-1635

<400> SEQUENCE: 97
gtacatgata atacagcaaa gatt                                            24
```